US006534067B1

(12) United States Patent
Estes

(10) Patent No.: US 6,534,067 B1
(45) Date of Patent: Mar. 18, 2003

(54) ROTAVIRUS ENTEROTOXIN ADJUVANT

(75) Inventor: Mary K. Estes, Friendswood, TX (US)

(73) Assignee: Baylor College of Medicine, Houston, TX (US)

( * ) Notice: Subject to any disclaimer, the term of this patent is extended or adjusted under 35 U.S.C. 154(b) by 0 days.

(21) Appl. No.: 09/687,698

(22) Filed: Oct. 13, 2000

Related U.S. Application Data

(60) Provisional application No. 60/159,390, filed on Oct. 14, 1999, now abandoned.

(51) Int. Cl.[7] ........................ A61K 47/00; A61K 45/00; A61K 39/12; A61K 35/15

(52) U.S. Cl. ................................ 424/278.1; 424/281.1; 424/186.1; 424/204.1; 424/215.1

(58) Field of Search ........................... 424/184.1, 215.1, 424/204.1, 201.1, 202.1, 203.1, 234.1, 241.1, 236.1, 196.11, 278.1, 281.1

(56) References Cited

PUBLICATIONS

Zhang et al. Journal of Virology. 2000; 74 (24): 11663–11670.*

Zhang et al. Journal of Virology. 1998; 72 (5): 3666–3672.*

Yuan et al. Journal of Virology. 2000; 74 (19): 8843–8853.*

Dickinson, B. L.; Dissociation of *Escherichia Coli* Heat–Labile Enterotoxin Adjuvanticity from ADP–Ribosyltransferase Activity; Infection and Immunity, May 1995 p. 1617–1623.

Ciarlet, M. et al. Species specificity and interspecies relatedness of NSP4 genetic groups by comparative NSP4 sequence analyses of animal rotaviruses; Arch Virol (2000) 145: 371–383.

Zhang, M., et al.; Mutations in Rotavirus Nonstructural Glycoprotein NSP4 are Associated with Altered Virus Virulence; Journal of Virology, May 1998, p. 3666–3672.

Mbawuike, I. N. et al.; Enhancement of the protective efficacy of inactivated influenza A virus vaccine in aged mice by IL–2 liposomes; Vaccine, vol.8 Aug. 1990, p. 347–352.

Mbawuike, I.N. and Wyde, P.; Induction of CD8 cytotoxic T cells by immunization with killed influenza virus and effect of cholera toxin B subunit; Vaccine, vol. 11, Issue 12, 1993, p. 1205–1213.

O'Neal, C. et al. Rotavirus 2/6 Viruslike Particles Administered Intranasally with Cholera Toxin, *Escherichia Coli* Heat–Labile Toxin (LT), and LT–R192G Induce Protection from Rotavirus Challenge; Journal of Virology, Apr. 1998, p. 3390–3393.

Morris, A. et al. NSP4 elicits age–dependent diarrhea and $Ca^{2+}$—mediated I—influx into intestinal crypts of CF mice; The American Physiological Society, 1999, p. G431–G444.

Ciarlet, M., et al., Subunit Rotavirus Vaccine Administered Parenterally to Rabbits Induces Active Protective Immunity; Journal of Virology, Nov. 1998, p. 9233–9246.

Peterson, J., et al. Cholera Toxin B Subunit Activates Arachidonic Acid Metabolism; Infecton and Immunity, Feb. 1999, p. 794–799.

PCT Notification of Transmittal of the International Search Report, Mar. 26, 2001.

Estes, Mary K.; Rotaviruses and Their Replication; Fields Virology, Third Edition; Lippincott–Raven Publishers, Philadelphia, 1996, pp. 1625–1654.

Ball, Judith M. et al., Age–Dependent Diarrhea Induced by a Rotaviral Nonstructural Glycoprotein; Science, Vo. 272, Apr. 5, 1996, pp. 101–104.

Coste, Alix, et al. "Nasal Immunization of Mice with Virus––Like Particles Protects Offspring against Rotavirus Diarrhea"; Journal of Virology, Oct. 2000, p. 8966–8971.

* cited by examiner

*Primary Examiner*—James Housel
*Assistant Examiner*—Shanon Foley
(74) *Attorney, Agent, or Firm*—Fulbright & Jaworski L.L.P.

(57) ABSTRACT

This invention relates to a method of potentiating an immune response by administering a viral enterotoxin or derivative as an adjuvant. More particularly it relates to administering a viral enterotoxin or derivative as an adjuvant and an antigen to a mucosal surface of a mammal.

17 Claims, 2 Drawing Sheets

ROTAVIRUS ENTEROTOXIN ADJUVANT

This application, claims priority to U.S. Provisional Application No. 60/159,390, now abandoned, which was filed Oct. 14, 1999.

The work herein was supported by grants from the United States Government. The United States Government may have certain rights in the invention.

FIELD OF THE INVENTION

This invention relates to the use of a viral enterotoxin or derivative as an adjuvant to enhance immune responses. More particularly it relates to the use of a viral enterotoxin or derivative as an adjuvant at mucosal surfaces to potentiate immune responses.

BACKGROUND OF THE INVENTION

Recombinant DNA technology has stimulated the pursuit of new, safe and effective vaccines. Disadvantages of recombinant vaccines include the need for large, repeated antigen doses, and a general failure to generate major histocompatibility complex (MHC) class I-restricted immune responses. To overcome these limitations, recombinant vaccines require the use of systemic- or mucosal-active immunostimulating agents, which are referred to as adjuvants (Gradon, et al., 1999). Immunopotentiation by adjuvants can result from quantitative enhancement of or qualitative alteration of components of the immune response compared to the immune response generated by an immunogen alone. Many compounds possess adjuvant properties but the only adjuvants currently licensed for use in humans by the Food and Drug Administration are aluminum salts (aluminum hydroxide or aluminum phosphate), which are relatively weak adjuvants approved only for systemic administration.

Development of mucosal vaccines has lagged behind systemic vaccines because of our limited knowledge of mucosal immunity and because no adjuvants have been licensed for use at mucosal surfaces. Mucosal vaccines and adjuvants would be advantageous because greater than 80% of pathogens enter the host at mucosal sites. Localized infections of the mucosa are the most common cause of mortality and morbidity in humans, and many pathogens that cause systemic infections gain access to the body at mucosal sites, including HIV, measles virus and polio virus (Gradon, et al., 1999). Therefore, a vaccine strategy that can potentially prevent the initial infection of the host is likely to be more successful than one that resolves infection before the disease ensues.

The bacterial enterotoxins, cholera toxin (CT) and *Escherichia coli* (*E. coli*) heat-labile enterotoxin (LT), are the most potent mucosal adjuvants described to date, but their enterotoxicity precludes their use in humans. Enterotoxins produced by *V. cholera, E. coli* and Salmonella have similar modes of action. Cholera toxin is a protein consisting of three polypeptides, A1, A2, and B subunits. The B subunit contains the binding site by which the cholera toxin binds to the ganglioside ($G_{M1}$), located on the cell membrane. The binding of the B subunit to the $G_{M1}$ receptor facilitates the translocation of the A subunit through the membrane. The A1 subunit activates the cellular enzyme, adenylcyclase, causing conversion of ATP to cyclic AMP (cAMP). The increased levels of cAMP result in secretion of water and electrolytes into the small intestine through interactions with cAMP-sensitive NaCl transport mechanisms. It has been suggested that the adjuvanticity of CT and LT is associated with their ability to increase gut permeability; therefore, facilitating access of luminal antigens to the gut mucosal immune system (Lycke, et al., 1991). In addition to modulating the mucosal immune system by stimulating synthesis of cAMP, it has also been suggested that CT can modulate the mucosal immune response by stimulating cellular syntheses of arachidonic acid metabolites (Peterson, et al., 1999).

Recent studies have examined the potential of CT and LT as mucosal adjuvants against a variety of bacterial and viral pathogens (Xu-Amano et al., 1994; Xu-Amno et al., 1993; Yamanoto et al., 1996 and Wu, et al., 1997). However, prior art indicates that as little as 5 μg of purified CT, administered orally, was sufficient to induce significant diarrhea in volunteers, while ingestion of 25 μg of CT elicited a full 20-liter cholera purge (Levine, et al., 1983). Similar studies have shown that LT induces fluid secretion at doses as low as 2.5 μg when administered in conjunction with a vaccine (Freytag and Clements, 1999).

A number of attempts have been made to alter the toxicity of LT and CT, most of which focus on eliminating activity of subunit A, which is associated with enterotoxicity. Recent studies have shown that site-directed mutagenesis to change any amino acid in CT or LT involved in the ADP-ribosylation results in a corresponding loss of toxicity and adjuvanticity (Yamamoto, et al., 1997 and Lycke, et al., 1992). Therefore, a logical conclusion is that ADP-ribosylation and induction of cAMP are essential for the enterotoxicity and adjuvanticity of LT and CT. As a result, a linkage has been established between enterotoxicity and adjuvanticity. Thus, there is a need for new, effective systemic and mucosal adjuvants suitable for human use to enhance the efficacy of vaccines to prevent life-threatening infections.

Although there are no sequence homologies between the rotavirus non-structural protein (NSP4) and any known bacterial enterotoxin, NSP4 by itself is immunogenic and antibodies against NSP4 protect neonatal mice against diarrhea induced by a rotavirus challenge (Ball, et al., 1996, and Zeng and Estes 1999). The mechanism of adjuvanticity of NSP4 and CT or LT mutants may be different. CT and LT activate cAMP which is required for adjuvanticity and enterotoxicity (Freytag and Clements, 1999, and Cheng, et al., 1999). In contrast, NSP4 enterotoxigenic activity results from chloride secretion stimulated by a signal transduction pathway that increases intracellular calcium through receptor-mediated phospholipase C (PLC) activation and inositol 1,4,5-triphosphate (IP3) (Ball, et al., 1996, and Dong, et al., 1997, and Morris et al., 1999). Activation of B and T lymphocytes also involves PLC and IP3 that stimulate increases in intracellular calcium (Freytag and Clements, 1999).

This invention demonstrates for the first time the use of NSP4 as a new adjuvant. It is noteworthy that although the prior art has used bacterial and aluminum compounds as adjuvants for potentiating an immune response, the use of a viral enterotoxin or derivative as an adjuvant has gone unrealized, suggesting that this invention is indeed novel and nonobvious.

SUMMARY OF THE INVENTION

An embodiment of the present invention is a method of potentiating an immune response against an antigen in an animal comprising the step of administering the antigen and an adjuvant wherein the adjuvant is a rotavirus enterotoxin or derivative thereof. Exemplary rotavirus enterotoxins include, but are not limited to the NSP4 group A genotypes A, B, C or D.

In specific embodiments, the adjuvant can be either a toxin or a non-toxic derivative. More particularly, a derivative of rotavirus can include, but is not limited to OSU NSP4-P138S or SA11 NSP4 aa 112-175.

In a preferred embodiment of the present invention, the antigen and the adjuvant are administered to an animal using standard methods. They can be co-administered or administered separately. Administration may be mucosal (e.g., intranasal, ocular, gastrointestinal, oral, rectal and genitourinary tract) or parenteral (e.g., intraperitoneal, intravenous, subcutaneous or muscular.) Animals that may be treated using the method of the invention include, but are not limited to humans, cows, horses, pigs, dogs, cats, sheep goats, rabbits, rats, mice, birds, chickens or fish.

Yet further, in specific embodiments, the immune response is systemic or mucosal.

A further embodiment of the present invention is that the antigen is rotavirus-like particles or influenza A. Additional antigens that can be used in the present invention include, but are not limited to cancer vaccines, viral vaccines, bacterial vaccines or parasitic vaccines.

A specific embodiment of the present invention is a method of potentiating an immune response against influenza A virus by administering to a mucosal surface an inactivated influenza A virus and an adjuvant. Specifically, the adjuvant is a rotavirus enterotoxin or a derivative thereof.

Another specific embodiment of the present invention is a method of potentiating an immune response to rotavirus-like particles by administering to a mucosal surface rotavirus-like particles and an adjuvant. In specific embodiments, the adjuvant is a rotavirus enterotoxin or a derivative thereof.

Other and further objects, features and advantages would be apparent and eventually more readily understood by reading the following specification and by reference to the company drawings forming a part thereof, or any examples of the present preferred embodiments of the invention are given for the purpose of the disclosure.

DETAILED DESCRIPTION OF THE INVENTION

Figure 1:
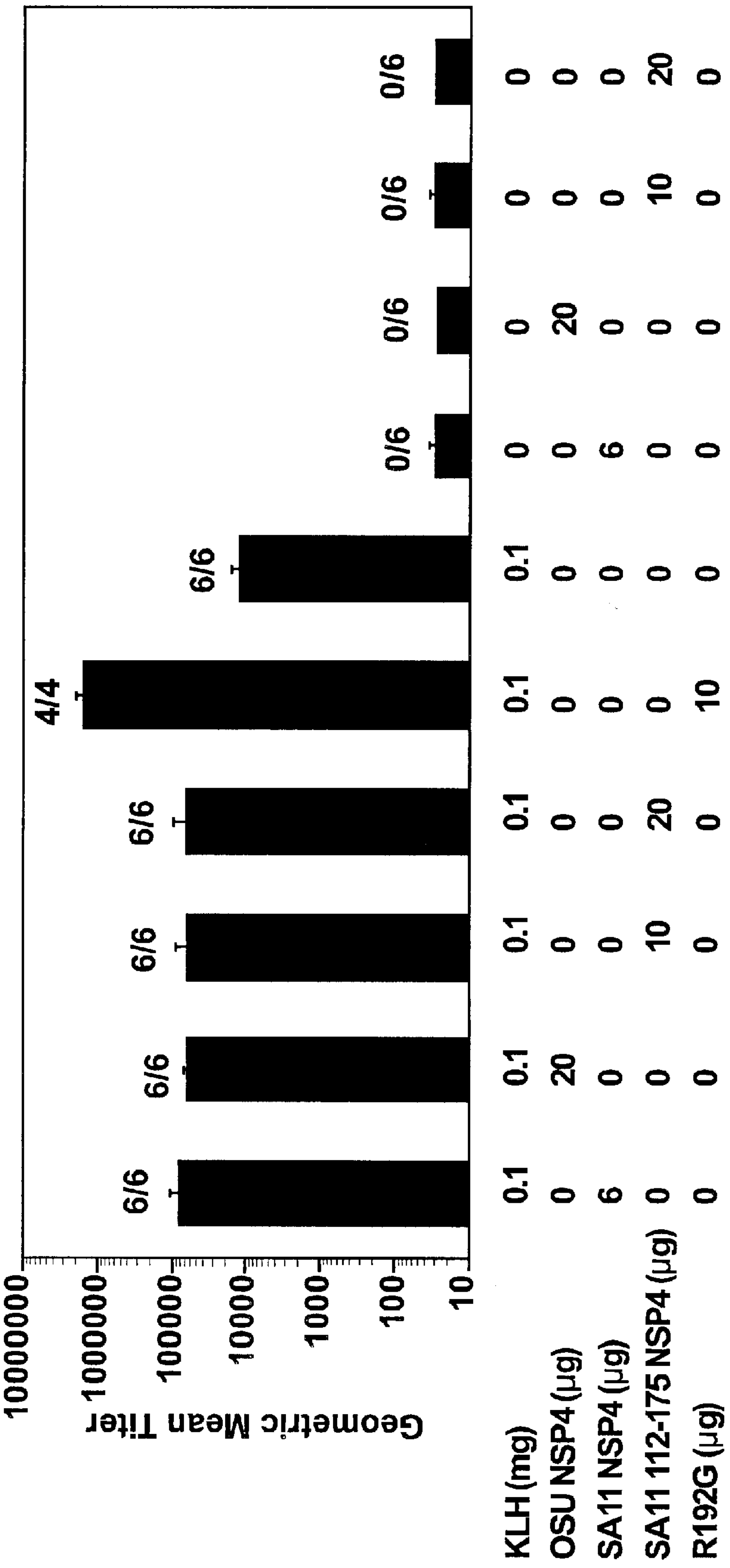
FIG. 1 shows the antibody responses evaluated by enzyme-linked immunosorbent assays (ELISAs) of serum immunoglobulin (IgG) immune response to keyhole limpet hemocyanin (KLH) administered intranasally in the presence or absence of rotavirus enterotoxin or LT.

It is readily apparent to one skilled in the art that various embodiments and modifications may be made to the invention disclosed in this application without departing from the scope and the spirit of the invention.

As used herein the specification, "a" or "an" may mean one or more. As used herein in the claim(s), when used in conjunction with the word "comprising", the words "a" or "an" may mean one or more than one. As used herein "another" may mean at least a second or more.

The term "adjuvant" as used herein is defined as an agent that, when administered with an antigen, enhances the immune response to the antigen. Specific adjuvants used herein include, but are not limited to rotavirus (groupA NSP4A, group A NSP4B, group A NSP4C, group A NSP4D and non-group A NSP4, e.g., group B or group C), rotavirus NSP4 derivatives, LT, LT derivatives, CT, CT derivatives and aluminum compounds.

The term "antibody" as used herein is defined as a serum immunoglobulin that has specific binding sites to combine with antigens.

The term "antigen" as used herein is defined as a molecule that provokes an immune response. This immune response may involve either antibody production, the activation of specific immunologically-competent cells, or both. An antigen can be derived from organisms. subunits of proteins/antigens, killed or inactivated whole cells or lysates. Exemplary organisms include but are not limited to, Helicobacters, Campylobacters, Clostridia, *Corynebacterium diphtheriae, Bordetella pertussis,* influenza virus, parainfluenza viruses, respiratory syncytial virus, *Borrelia burgdorfei,* Plasmodium, herpes simplex viruses, human immunodeficiency virus, papilloma virus, *Vibrio cholera, E. coli*, measles virus, rotavirus, shigella, *Salmonella typhi, Neisseria gonorrhea*. Therefore, a skilled artisan realizes that any marcromolecule, including virtually all proteins, can serve as antigens.

The term "cDNA" is intended to refer to DNA prepared using messenger RNA (mRNA) as template.

The term "derivative" as used herein is defined as an altered form of a toxin or a protein. Exemplary derivatives as contained herein include, but are not limited to OSU NSP4-P138S or LT-R192G. One of skilled in the art recognizes that a derivative as defined herein is an altered or mutated toxin or protein. Such alterations or mutations are produced using standard techniques well known in the art, e.g., site-directed mutagenesis or chemical mutagenesis.

The term "DNA" as used herein is defined as deoxyribonucleic acid.

The term "enterotoxin" as used herein is defined as a toxin which affects the intestinal mucosal cells causing secretion of fluid into the intestinal lumen which leads to the symptoms of diarrhea.

The term "functionally equivalent codon" is used herein is to refer to codons that encode the same amino acid, such as the six codons for arginine or serine, and also refers to codons that encode biologically equivalent amino acids.

The term "immunoglobulin" or "Ig", as used herein is defined as a class of proteins which functions as antibodies. Two members in this class of proteins are IgA and IgG. IgA functions as the primary antibody that is present in body secretions, such as saliva, tears, breast milk, gastrointestinal secretions and mucus secretions of the respiratory and genitourinary tracts. IgG functions as the most common circulating antibody.

The term "non-toxic derivative" or "toxoid" as used herein is defined as a derivative of a toxin, which has limited toxicity, but retains complete adjuvanticity. One of skilled in the art is cognizant that "limited toxicity" as used herein refers to the quality of retaining biological activity without being poisonous.

The term "polynucleotide" as used herein is defined as a chain of nucleotides. Furthermore, nucleic acids are polymers of nucleotides. Thus, one of skill in the art is cognizant that nucleic acids and polynucleotides as used herein are interchangeable.

The term "polypeptide" as used herein is defined as a chain of amino acid residues, usually having a defined squences. As used herein the term polypeptide is mutually inclusive of the terms "peptides" and "proteins".

The term "recombinant DNA" as used herein is defined as DNA produced by joining pieces of DNA from different sources.

The term "recombinant polypeptide" as used herein is defined as a hybrid protein produced by using recombinant DNA methods.

The term "RNA" as used herein is defined as ribonucleic acid.

The term "toxin" as used herein is defined as a noxious or poisonous substance that is produced by a pathogen and results in damage to the infected host. Toxins that are considered cell bound and released only upon lysis of the cell are referred to as endotoxins. Toxins that are released extracellulary as the organism/pathogen grows are referred to as exotoxins.

The term "vaccine" as used herein is defined as material used to provoke an immune response (e.g., the production of antibodies) on administration of the materials and thus conferring immunity.

The term "vector" is used to refer to a carrier polynucleotide molecule into which a polynucleotide sequence can be inserted for introduction into a cell where it can be replicated.

The term "virus" as used herein is defined as a particle consisting of nucleic acid (RNA or DNA) enclosed in a protein coat, with or without an outer lipid envelope, which is only capable of replicating within a whole cell and spreading from cell to cell.

One specific embodiment of the present invention is a method of potentiating an immune response against an antigen in an animal comprising the step of administering to the animal the antigen and the adjuvant wherein the adjuvant is a rotavirus enterotoxin or a derivative thereof. It is contemplated that the immune response is systemic or mucosal.

In another specific embodiment of the present invention the adjuvant and the antigen are administered to mucosal surfaces (e.g., intranasal, ocular, gastrointestinal, oral, rectal and genitourinary tract). A skilled artisan recognizes the importance of developing mucosal immunization methods because the majority of deaths from infectious diseases are caused by organisms that first make contact with and either colonize or cross the mucosal surface to infect the host. Therefore, a vaccine that does not prevent the initial infection of the host will unlikely succeed in resolving the infection before the disease ensues. Mucosal immunization induces IgA antibodies, which are directed against specific pathogens of mucosal surfaces. It is suggested that greater than 80% of all the antibodies produced in mucosal-associated lymphoid tissues may block attachment of bacteria and viruses. This blockade neutralizes bacterial toxins and inactivates invading viruses inside the epithelial cells. Therefore, a skilled artisan can readily recognize that mucosal immunization would actually prevent the initial infection resulting in a decrease in the morbidity caused by pathogens.

An additional embodiment includes administration of the antigen and the adjuvant via parenteral routes (e.g. intraperitoneal, intravenous, subcutaneous or muscular). To demonstrate the range of applicability, different routes of immunization are tested. The ability of the adjuvant to enhance the immune response to multiple antigens and by more than one route of immunization illustrate the potency and efficiency of the adjuvant. One skilled in the art realizes that any given adjuvant may be more effective with certain antigens via different routes of immunization. Therefore, it is necessary to determine the range of potency and efficiency of the adjuvant.

Yet further, in specific embodiments, the antigen and adjuvant are co-administered or administered sequentially.

In other specific embodiments, the antigen is rotavirus-like particles or influenza A antigen. Other exemplary antigens include, but are not limited to cancer vaccines, viral vaccines or bacterial vaccines. In certain embodiments, an antigenic composition's may be chemically coupled to a carrier or recombinantly expressed with an immunogenic carrier peptide or polypeptide (e.g., a antigen-carrier fusion peptide or polypeptide) to enhance an immune reaction. Exemplary and preferred immunogenic carrier amino acid sequences include hepatitis B surface antigen, keyhole limpet hemocyannin (KLH) and bovine serum albumin (BSA). Other albumins such as ovalbumin, mouse serum albumin or rabbit serum albumin also can be used as immunogenic carrier proteins. Means for conjugating a polypeptide or peptide to a immunogenic carrier protein are well known in the art and include, for example, glutaraldehyde, m-maleimidobenzoyl-N-hydroxysuccinimide ester, carbodiimide and bis-biazotized benzidine.

Another embodiment of the present invention is that the adjuvant can be an enterotoxin or a non-toxic derivative. Specific enterotoxins used herein include, but are not limited to rotavirus (groupA NSP4A, group A NSP4B, group A NSP4C, group A NSP4D and non-group A NSP4), rotavirus NSP4 derivatives, LT, LT derivatives, CT, or CT derivatives. One of skill in the art is cognizant of the nomenclature of rotaviruses. For example, rotaviruses are classified into groups A–F of which the viruses associated with the most severe diseases are within group A. The NSP4 genes of group A are further classified into groups A–D based on phylogenetic analyses (Ciarlet, et al., 2000). Thus, in the present invention it is also contemplated that non-group A NSP4 proteins may be used as adjuvants. Non-group A NSP4 proteins, e.g., group B, have been shown to mobilize intracellular calcium (Tian, et al., 1994). Non-group A NSP4 proteins include, but are not limited to group B, group C, group D, group E or group F.

The toxins used in the present invention may be purified from standard bacterial or viral cultures or produced using standard DNA recombinant methods and expression systems or chemical modifications. Since the 1970's, a skilled artisan has used DNA technology to synthesize and manipulate nucleic acids. These DNA methods are standard techniques in the art.

Furthermore, derivatives of toxins included in the present invention may contain insertions, substitutions and/or deletions of the wild-type sequence using standard DNA recombinant methods, e.g., site-directed mutagenesis. Exemplary derivatives include without limitations OSU NSP4-P138S, which is a single amino acid substitution at position 138 or SA11 NSP4 aa 112-175, which is a deletion of the first 111 amino acids. Standard chemical modifications of amino acids, which are critical for toxicity, but not adjuvanticity, may be used to generate non-toxic derivatives or toxoids. One of skill in the art is cognizant of the specific moiety or moieties that are associated with toxicity and adjuvanticity in toxins. Thus, the moiety or moieties associated with toxicity can be altered using standard mutagenesis techniques resulting in a non-toxic derivative or toxoid that is an adjuvant. An example of this dissociation of toxicity and adjuvanticity in a toxin is provided in the reference by Dickinson and Clements, *Infection and Immunity* (1995) 63:1617–1623, which is herein incorporated by reference in its entirety. Thus, a skilled artisan can appreciate the examples provided herein and extrapolate to other toxins to dissociate the moieties associated with toxicity and adjuvanticity to produce a non-toxic derivative or toxoid.

Other standard mutagenesis techniques that can be used in the present invention include the use of reagents which modify lysine, tyrosine or SH-containing amino acids. Furthermore, standard photoaffinity labeling methods which use azido-linked substrate derivatives, can be covalently linked to the toxin active sites by ultraviolet irradiation.

Mutagenesis

Mutations can arise spontaneously as a result of events such as errors in the fidelity of DNA replication or the movement of transposable genetic elements (transposons) within the genome. They also are induced following exposure to chemical or physical mutagens. Such mutation-inducing agents include ionizing radiation, ultraviolet light and a diverse array of chemical such as alkylating agents and polycyclic aromatic hydrocarbons all of which are capable of interacting either directly or indirectly (generally following some metabolic biotransformations) with nucleic acids. The DNA lesions induced by such environmental agents may lead to modifications of base sequence when the affected DNA is replicated or repaired and thus to a mutation. Mutation also can be site-directed through the use of particular targeting methods.

A. Insertional Mutagenesis

Insertional mutagenesis is based on the inactivation of a gene via insertion of a known DNA fragment. Because it involves the insertion of some type of DNA fragment, the mutations generated are generally loss-of-function, rather than gain-of-function mutations. However, there are several examples of insertions generating gain-of-function mutations (Oppenheimer et al., 1991). Insertional mutagenesis has been very successful in bacteria and Drosophila (Cooley et al., 1988) and recently has become a powerful tool in corn (Schmidt et al., 1987); Arabidopsis; (Marks et al., 1991; Koncz et al., 1990); and Antirrhinum (Sommer et al., 1990).

Transposable genetic elements are DNA sequences that can move (transpose) from one place to another in the genome of a cell. The first transposable elements to be recognized were the Activator/Dissociation elements of *Zea mays* (McClintock, 1957). Since then, they have been identified in a wide range of organisms, both prokaryotic and eukaryotic.

Transposable elements in the genome are characterized by being flanked by direct repeats of a short sequence of DNA that has been duplicated during transposition and is called a target site duplication. Virtually all transposable elements whatever their type, and mechanism of transposition, make such duplications at the site of their insertion. In some cases the number of bases duplicated is constant, in other cases it may vary with each transposition event. Most transposable elements have inverted repeat sequences at their termini. These terminal inverted repeats may be anything from a few bases to a few hundred bases long and in many cases they are known to be necessary for transposition.

Prokaryotic transposable elements have been most studied in *E. coli* and Gram negative bacteria, but also are present in Gram positive bacteria. They are generally termed insertion sequences if they are less than about 2 kB long, or transposons if they are longer. Bacteriophages such as mu and D108, which replicate by transposition, make up a third type of transposable element. Elements of each type encode at least one polypeptide a transposase, required for their own transposition. Transposons often further include genes coding for function unrelated to transposition, for example, antibiotic resistance genes.

Transposons can be divided into two classes according to their structure. First, compound or composite transposons have copies of an insertion sequence element at each end, usually in an inverted orientation. These transposons require transposases encoded by one of their terminal IS elements. The second class of transposon have terminal repeats of about 30 base pairs and do not contain sequences from IS elements.

Transposition usually is either conservative or replicative, although in some cases it can be both. In replicative transposition, one copy of the transposing element remains at the donor site, and another is inserted at the target site. In conservative transposition, the transposing element is excised from one site and inserted at another.

Eukaryotic elements also can be classified according to their structure and mechanism of transposition. The primary distinction is between elements that transpose via an RNA intermediate, and elements that transpose directly from DNA to DNA.

Elements that transpose via an RNA intermediate often are referred to as retrotransposons, and their most characteristic feature is that they encode polypeptides that are believed to have reverse transcriptionase activity. There are two types of retrotransposon. Some resemble the integrated proviral DNA of a retrovirus in that they have long direct repeat sequences, long terminal repeats (LTRs), at each end. The similarity between these retrotransposons and proviruses extends to their coding capacity. They contain sequences related to the gag and pol genes of a retrovirus, suggesting that they transpose by a mechanism related to a retroviral life cycle. Retrotransposons of the second type have no terminal repeats. They also code for gag- and pol-like polypeptides and transpose by reverse transcription of RNA intermediates, but do so by a mechanism that differs from that or retrovirus-like elements. Transposition by reverse transcription is a replicative process and does not require excision of an element from a donor site.

Transposable elements are an important source of spontaneous mutations, and have influenced the ways in which genes and genomes have evolved. They can inactivate genes by inserting within them, and can cause gross chromosomal rearrangements either directly, through the activity of their transposases, or indirectly, as a result of recombination between copies of an element scattered around the genome. Transposable elements that excise often do so imprecisely and may produce alleles coding for altered gene products if the number of bases added or deleted is a multiple of three.

Transposable elements themselves may evolve in unusual ways. If they were inherited like other DNA sequences, then copies of an element in one species would be more like copies in closely related species than copies in more distant species. This is not always the case, suggesting that transposable elements are occasionally transmitted horizontally from one species to another.

B. Chemical Mutagenesis

Chemical mutagenesis offers certain advantages, such as the ability to find a full range of mutant alleles with degrees of phenotypic severity, and is facile and inexpensive to perform. The majority of chemical carcinogens produce mutations in DNA. Benzo[a]pyrene, N-acetoxy-2-acetyl aminofluorene and aflotoxin B1 cause GC to TA transversions in bacteria and mammalian cells. Benzo[a]pyrene also can produce base substitutions such as AT to TA. N-nitroso compounds produce GC to AT transitions. Alkylation of the O4 position of thymine induced by exposure to n-nitrosoureas results in TA to CG transitions. Other chemical reagents can modify lysine, tyrosine or SH-containing amino acids resulting in mutated proteins.

C. Radiation Mutagenesis

The integrity of biological molecules is degraded by the ionizing radiation. Adsorption of the incident energy leads to the formation of ions and free radicals, and breakage of some covalent bonds. Susceptibility to radiation damage appears quite variable between molecules, and between different crystalline forms of the same molecule. It depends on the total accumulated dose, and also on the dose rate (as once free radicals are present, the molecular damage they cause depends on their natural diffusion rate and thus upon real time). Damage is reduced and controlled by making the sample as cold as possible.

Ionizing radiation causes DNA damage and cell killing, generally proportional to the dose rate. Ionizing radiation has been postulated to induce multiple biological effects by direct interaction with DNA, or through the formation of free radical species leading to DNA damage (Hall, 1988).

In the present invention, the term ionizing radiation means radiation comprising particles or photons that have sufficient energy or can produce sufficient energy via nuclear interactions to produce ionization (gain or loss of electrons). An exemplary and preferred ionizing radiation is an x-radiation. The amount of ionizing radiation needed in a given cell generally depends upon the nature of that cell. Typically, an effective expression-inducing dose is less than a dose of ionizing radiation that causes cell damage or death directly. Means for determining an effective amount of radiation are well known in the art.

In a certain embodiments, an effective expression inducing amount is from about 2 to about 30 Gray (Gy) administered at a rate of from about 0.5 to about 2 Gy/minute. Even more preferably, an effective expression inducing amount of ionizing radiation is from about 5 to about 15 Gy. In other embodiments, doses of 2–9 Gy are used in single doses. An effective dose of ionizing radiation may be from 10 to 100 Gy, with 15 to 75 Gy being preferred, and 20 to 50 Gy being more preferred.

Any suitable means for delivering radiation to a tissue may be employed in the present invention in addition to external means. For example, radiation may be delivered by first providing a radiolabeled antibody that immunoreacts with an antigen of the tumor, followed by delivering an effective amount of the radiolabeled antibody to the tumor. In addition, radioisotopes may be used to deliver ionizing radiation to a tissue or cell.

D. In vitro Scanning Mutagenesis

Random mutagenesis also may be introduced using error prone PCR (Cadwell and Joyce, 1992). The rate of mutagenesis may be increased by performing PCR in multiple tubes with dilutions of templates.

One particularly useful mutagenesis technique is alanine scanning mutagenesis in which a number of residues are substituted individually with the amino acid alanine so that the effects of losing side-chain interactions can be determined, while minimizing the risk of large-scale perturbations in protein conformation (Cunningham et al., 1989).

In recent years, techniques for estimating the equilibrium constant for ligand binding using minuscule amounts of protein have been developed (Blackburn et al., 1991; U.S. Pat. Nos. 5,221,605 and 5,238,808). The ability to perform functional assays with small amounts of material can be exploited to develop highly efficient, in vitro methodologies for the saturation mutagenesis of antibodies. The inventors bypassed cloning steps by combining PCR mutagenesis with coupled in vitro transcription/translation for the high throughput generation of protein mutants. Here, the PCR products are used directly as the template for the in vitro transcription/translation of the mutant single chain antibodies. Because of the high efficiency with which all 19 amino acid substitutions can be generated and analyzed in this way, it is now possible to perform saturation mutagenesis on numerous residues of interest, a process that can be described as in vitro scanning saturation mutagenesis (Burks et al., 1997).

In vitro scanning saturation mutagenesis provides a rapid method for obtaining a large amount of structure-function information including: (i) identification of residues that modulate ligand binding specificity, (ii) a better understanding of ligand binding based on the identification of those amino acids that retain activity and those that abolish activity at a given location, (iii) an evaluation of the overall plasticity of an active site or protein subdomain, (iv) identification of amino acid substitutions that result in increased binding.

E. Random Mutagenesis by Fragmentation and Reassembly

A method for generating libraries of displayed polypeptides is described in U.S. Pat. No. 5,380,721. The method comprises obtaining polynucleotide library members, pooling and fragmenting the polynucleotides, and reforming fragments therefrom, performing PCR amplification, thereby homologously recombining the fragments to form a shuffled pool of recombined polynucleotides.

F. Site-Directed Mutagenesis

Structure-guided site-specific mutagenesis represents a powerful tool for the dissection and engineering of protein-ligand interactions (Wells, 1996, Braisted et al., 1996). The technique provides for the preparations and testing of sequence variants by introducing one or more nucleotide sequence changes into a selected DNA.

Site-specific mutagenesis uses specific oligonucleotide sequences which encode the DNA sequence of the desired mutation, as well as a sufficient number of adjacent, unmodified nucleotides. In this way, a primer sequence is provided with sufficient size and complexity to form a stable duplex on both sides of the deletion junction being traversed. A primer of about 17 to 25 nucleotides in length is preferred, with about 5 to 10 residues on both sides of the junction of the sequence being altered.

The technique typically employs a bacteriophage vector that exists in both a single-stranded and double-stranded form. Vectors useful in site-directed mutagenesis include vectors such as the M13 phage. These phage vectors are commercially available and their use is generally well known to those skilled in the art. Double-stranded plasmids are also routinely employed in site-directed mutagenesis, which eliminates the step of transferring the gene of interest from a phage to a plasmid.

In general, one first obtains a single-stranded vector, or melts two strands of a double-stranded vector, which includes within its sequence a DNA sequence encoding the desired protein or genetic element. An oligonucleotide primer bearing the desired mutated sequence, synthetically prepared, is then annealed with the single-stranded DNA preparation, taking into account the degree of mismatch when selecting hybridization conditions. The hybridized product is subjected to DNA polymerizing enzymes such as *E. coli* polymerase I (Klenow fragment) in order to complete the synthesis of the mutation-bearing strand. Thus, a heteroduplex is formed, wherein one strand encodes the original non-mutated sequence, and the second strand bears the desired mutation. This heteroduplex vector is then used to transform appropriate host cells, such as *E. coli* cells, and clones are selected that include recombinant vectors bearing the mutated sequence arrangement.

Comprehensive information on the functional significance and information content of a given residue of protein can best be obtained by saturation mutagenesis in which all 19 amino acid substitutions are examined. The shortcoming of this approach is that the logistics of multiresidue saturation mutagenesis are daunting (Warren et al., 1996, Brown et al., 1996; Zeng et al., 1996; Burton and Barbas, 1994; Yelton et al., 1995; Jackson et al., 1995; Short et al., 1995; Wong et al., 1996; Hilton et al., 1996). Hundreds, and possibly even thousands, of site specific mutants must be studied. However, improved techniques make production and rapid screening of mutants much more straightforward. See also, U.S. Pat. Nos. 5,798,208 and 5,830,650, for a description of "walk-through" mutagenesis.

Other methods of site-directed mutagenesis are disclosed in U.S. Pat. Nos. 5,220,007; 5,284,760; 5,354,670; 5,366,878; 5,389,514; 5,635,377; and 5,789,166.

One skilled in the art will readily understand that in making fragments or derivatives of toxins for use in the methods and compositions of the invention, it is desirable to maintain adjuvanticity and limit the toxicity or poisonous quality of the toxin.

Nucleic Acids Encoding NSP4

In certain embodiments, one group of adjuvants of the present invention are those that can be encoded by a nucleic acid (e.g., DNA or RNA). It is contemplated that such adjuvants may be encoded in an expression vector encoding the antigen, or in a separate vector or other construct. These nucleic acids encoding the adjuvants can be delivered directly, such as for example with lipids or liposomes.

Specifically, nucleic acids according to the present invention may encode an entire NSP4 gene, a domain of NSP4, or any other fragment of NSP4 as set forth herein. The nucleic acid may be derived from genomic DNA, i.e., cloned directly from the genome of a particular organism. The following sequences are sequences corresponding to NSP4 genes that are classified in the group A rotaviruses and are within the scope of the invention and are referenced with the corresponding GenBank Accession Numbers: ALA (SEQ.ID.NO: 1, AF144792); C-11 (SEQ.ID.NO:2, AF144793); R-2 (SEQ.ID.NO:3, AF144794); BAP-2 (SEQ.ID.NO:4, AF144795); BAPwt (SEQ.ID.NO:5, AF144796);, A253 (SEQ.ID.NO:6, AF144797); A131 (SEQ.ID.NO:7, AF144798); A411 (SEQ.ID.NO:8, AF144799); A34 (SEQ.ID.NO:9, AF165219); H-1 (SEQ.ID.NO: 10, AF144801); FI-23 (SEQ.ID.NO:11, AF144802); FI-14 (SEQ.ID.NO:12, AF144803); BRV033 (SEQ.ID.NO:13, AF144804); B223 (SEQ.ID.NO:14, AF144805); CU-1 (SEQ.ID.NO:15, AF144806); OSU (SEQ.ID.NO:16, D88831); and SA11 (SEQ.ID.NO:17, AF0871678).

Also within the scope of the invention is the NSP4 sequences of the different virus strains and groups which are discussed in Ciarlet, et al., 2000, which is hereby incorporated by reference. Thus any strain can be used to incorporate the NSP4 sequence into vectors to make recombinant molecules.

In further embodiments, the following NSP4 sequences that are classified in the non-group A rotavirus NSP4s are within the scope of the present invention and are referenced with the corresponding GenBank Accession Numbers: group B IDIR (SEQ.ID.NO: 18, U03557); group C (SEQ.ID.NO: 19 X83967); group C (SEQ.ID.NO: 20, D88353) and group C (SEQ.ID.NO: 21, L12391).

In preferred embodiments, however, the nucleic acid would comprise complementary DNA (cDNA). The genome of rotavirus is a double-stranded RNA. Thus, one of skill in the art is cognizant that cDNA is produced of the RNA genome to allow for cloning into vectors. Typically, RT-PCR is used to generate copies of cDNA from RNA.

A. Vectors for Cloning, Gene Transfer and Expression

Within certain embodiments, expression vectors are employed to express a NSP4 peptide product or derivative thereof, which can then be purified and, for example, be used to as an adjuvant. Expression requires that appropriate signals be provided in the vectors, and which include various regulatory elements, such as enhancers/promoters from both viral and mammalian sources that drive expression of the genes of interest in host cells.

1. Regulatory Elements

In certain embodiments, the polynucleotide sequence encoding a gene product is under transcriptional control of a promoter. A promoter refers to a DNA sequence recognized by the synthetic machinery of the cell, or introduced synthetic machinery, required to initiate the specific transcription of a gene. One of skill in the art further recognizes that under transcriptional control means that the promoter is in the correct location and orientation in relation to the polynucleotide sequence to control RNA polymerase initiation and expression of the gene.

In certain embodiments, the bacterial phage promoters are used to obtain high-level expression of the coding sequence of interest. Yet further other viral or mammalian promoters may be used. All of these promoters systems are well-known in the art.

2. Selectable Markers

In certain embodiments of the invention, the cells contain polynucleotide sequence constructs of the present invention. A cell may be identified in vitro or in vivo by including a marker in the expression construct. Such markers would confer an identifiable change to the cell permitting easy identification of cells containing the expression construct. Usually the inclusion of a drug selection marker aids in cloning and in the selection of transformants, for example, genes that confer resistance to neomycin, puromycin, hygromycin, DHFR, GPT, zeocin and histidinol are useful selectable markers. Alternatively, enzymes such as herpes simplex virus thymidine kinase (tk) or chloramphenicol acetyltransferase (CAT) may be employed. Immunologic markers also can be employed. The selectable marker employed is not believed to be important, so long as it is capable of being expressed simultaneously with the polynucleotide sequence encoding a gene product. Further examples of selectable markers are well known to one of skill in the art.

3. Vectors

In certain embodiments, vectors may be employed to produce the adjuvants of the present invention. A polynucleotide sequence can be exogenous, which means that it is foreign to the cell into which the vector is being introduced or that the sequence is homologous to a sequence in the cell but in a position within the host cell polynucleotide sequence in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques, which are described in Maniatis et al., 1988 and Ausubel et al., 1994, both incorporated herein by reference.

An expression vector is a vector containing a polynucleotide sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to polynucleotide sequences necessary for the transcription and possibly translation of an operably linked coding sequence in a particular host organism. In addition to control sequences that govern transcription and translation, vectors and expression vectors may contain polynucleotide sequences that serve other functions as well and are described infra.

4. Expression Systems

Numerous expression systems exist that comprise at least a part or all of the compositions discussed above. Prokaryote- and/or eukaryote-based systems can be employed for use with the present invention to produce polynucleotide sequences, or their cognate polypeptides, proteins and peptides. Many such systems are commercially and widely available.

The insect cell/baculovirus system can produce a high level of protein expression of a heterologous polynucleotide segment, such as described in U.S. Pat. Nos. 5,871,986, 4,879,236, both herein incorporated by reference, and which can be bought, for example, under the name MAXBAC® 2.0 from INVITROGEN® and BACPACK™ BACULOVIRUS EXPRESSION SYSTEM FROM CLONTECH®.

Other examples of expression systems include STRATAGENE®'s COMPLETE CONTROL™ Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a polynucleotide sequence or its cognate polypeptide, protein, or peptide.

5. Delivery of Expression Vectors

There are a number of ways in which expression vectors may be introduced into cells. In certain embodiments of the invention, the expression construct comprises a virus or engineered construct derived from a viral genome. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986). These have a relatively low capacity for foreign DNA sequences and have a restricted host spectrum. Furthermore, their oncogenic potential and cytopathic effects in permissive cells raise safety concerns. They can accommodate only up to 8 kB of foreign genetic material but can be readily introduced in a variety of cell lines and laboratory animals (Nicolas and Rubenstein, 1988; Temin, 1986).

Several non-viral methods for the transfer of expression constructs into cultured mammalian cells are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al., 1990), and receptor-mediated transfection (Wu and Wu, 1987; Wu and Wu, 1988). Some of these techniques may be successfully adapted for in vivo or ex vivo use.

6. Host Cells

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous polynucleotide sequence, "host cell" refers to a prokaryotic or eukaryotic cell, and it includes any transformable organisms that is capable of replicating a vector and/or expressing a heterologous gene encoded by a vector. A host cell can, and has been, used as a recipient for vectors. A host cell may be "transfected" or "transformed," which refers to a process by which exogenous polynucleotide is transferred or introduced into the host cell. A transformed cell includes the primary subject cell and its progeny.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the polynucleotides encoded by vectors and their cognate polypeptides, proteins, or peptides.

Polypeptides, Peptides or Proteins

The present invention also relates to the production and/or purification of polypeptides, peptides or proteins that are used as an adjuvant. The peptides of the invention can be synthesized in solution or on a solid support in accordance with conventional techniques. Various automatic synthesizers are commercially available and can be used in accordance with known protocols. See, for example, Stewart and Young, (1984); Tam et al., (1983); Merrifield, (1986); and Barany and Merrifield (1979), each incorporated herein by reference. Short peptide sequences, or libraries of overlapping peptides, usually from about 6 up to about 35 to 50 amino acids, which correspond to the selected regions described herein, can be readily synthesized and then screened in screening assays designed to identify reactive peptides. Alternatively, recombinant DNA technology may be employed wherein a polynucleotide sequence which encodes a peptide of the invention is inserted into an expression vector, transformed or transfected into an appropriate host cell and cultivated under conditions suitable for expression.

A. Purification of Proteins

In further embodiments, it may be desirable to purify the polypeptides, peptide, proteins or variants thereof. Protein purification techniques are well known to those of skill in the art. These techniques involve, at one level, the crude fractionation of the cellular milieu to polypeptide and nonpolypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography or even HPLC.

Certain aspects of the present invention concern the purification, and in particular embodiments, the substantial purification, of an encoded protein or peptide. The term purified protein or peptide as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, purified will refer to a protein or peptide composition that has been subjected to fractionation to remove various other components, and which composition substantially retains its expressed biological activity. Where the term substantially purified is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in the most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

A particular type of affinity chromatography useful in the purification of carbohydrate containing compounds is lectin affinity chromatography. Lectins are a class of substances that bind to a variety of polysaccharides and glycoproteins. Lectins are usually coupled to agarose by cyanogen bromide. Conconavalin A coupled to Sepharose was the first material of this sort to be used and has been widely used in the isolation of polysaccharides and glycoproteins other lectins that have been include lentil lectin, wheat germ agglutinin which has been useful in the purification of N-acetyl glucosaminyl residues and Helix pomatia lectin. Lectins themselves are purified using affinity chromatography with carbohydrate ligands. Lactose has been used to purify lectins from castor bean and peanuts; maltose has been useful in extracting lectins from lentils and jack bean; N-acetyl-D galactosamine is used for purifying lectins from soybean; N-acetyl glucosaminyl binds to lectins from wheat germ; D-galactosamine has been used in obtaining lectins from clams and L-fucose will bind to lectins from lotus.

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography. The generation of antibodies that would be suitable for use in accord with the present invention is discussed below.

Fusion Proteins

Also contemplated in the present invention is a fusion protein or chimera. This molecule generally has all or a substantial portion of the native molecule, linked at the N- or C-terminus, to all or a portion of a second polypeptide. The second polypeptide may include a second enterotoxin or another protein that comprises adjuvant activity. Yet further, the second polypeptide may comprise the antigen of interest. For example, a fusion protein can comprise NSP4 protein and influenza A antigen. Another useful fusion includes the addition of an immunologically active domain, such as an antibody epitope, to facilitate purification of the fusion protein. Inclusion of a cleavage site at or near the fusion junction will facilitate removal of the extraneous polypeptide after purification.

Dosage and Formulation

The adjuvants of this invention can be formulated and administered to potentiate the immune response in the body of an animal. They can be administered by any conventional means available for use in conjunction with potential vaccines. They can be administered alone, but are generally administered with a pharmaceutical carrier selected on the basis of the chosen route of administration and standard pharmaceutical practice.

The adjuvant can be administered in liquid dosage forms such as elixirs, syrups, emulsions and suspensions. The adjuvant can also be formulated for administration parenterally by injection, rapid infusion, nasopharyngeal absorption or dermoabsorption. The adjuvant may be administered intramuscularly, intravenously or as a suppository.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Suitable pharmaceutical carriers are described in Remington's Pharmaceutical Sciences, a standard reference text in this field.

Accordingly, the pharmaceutical composition of the present invention may be delivered via various routes to various sites in the animal to achieve a particular effect. One skilled in the art will recognize that although more than one route can be used for administration, a particular route can provide a more immediate and more effective reaction than another route. Local or systemic delivery can be accomplished by administration comprising application or installation of the formulation into body cavities inhalation or insufflation of an aerosol, or by parenteral introduction, comprising intramuscular, intravenous, intraperitoneal, subcutaneous, intradermal, as well as topical administration.

The adjuvant of the present invention can be provided in unit dosage form wherein each dosage unit, e.g., a teaspoonful, solution, or suppository, contains a predetermined amount of the adjuvant, alone or in appropriate combination with a vaccine. The term "unit dosage form" as used herein refers to physically discrete units suitable as unitary dosages for animals, each unit containing a predetermined quantity of the adjuvant, alone or in combination with a vaccine, calculated in an amount sufficient to produce the desired effect, in association with a pharmaceutically acceptable diluent, carrier, or vehicle, where appropriate. The specifications for the unit dosage forms of the present invention depend on the particular effect to be achieved and the particular pharmacodynamics associated with the pharmaceutical composition in the particular host.

These methods described herein are by no means all inclusive, and further methods to suit the specific application will be apparent to the ordinary skilled artisan. Moreover, the effective amount of the compositions can be further approximated through analogy to compounds known to exert the desired affect.

The following examples are offered by way of example, and are not intended to limit the scope of the invention in any manner.

EXAMPLE 1

Animal Vaccination and Pathogen Challenge

Standard protocols have been established to immunize animals. Animals can be immunized orally, intranasally or parentally with test antigens (Ciarlet, et al., 1998, O'Neal, et al., 1998, Mbawuike, et al., 1990, Mbawuike, et al., 1993, Ciarlet, et al., 2000, and Ciarlet, et al., 1999b). The regime for immunization can vary depending on the route of administration, the type of vaccine administered or the amount of the vaccine administered. To confer immunity (e.g., specific antibody production), the animals are challenged with a pathogen. For example, an influenza vaccine was administered at sub-optimal doses as an intraperitoneal injection to mice. Four to six weeks following the vaccination, mice were infected or challenged with influenza virus and mortality was recorded (Mbawuike, et al., 1990). In another example, rabbits were vaccinated twice intramuscularly at 0 and 21 or 28 days with a given volume of rotavirus cell lysate. After 56–69 days postvaccination, the rabbits were challenged with rotavirus and serumand fecal samples were collected to measure antirotavirus antibodies (Ciarlet, et al., 1998).

A skilled artisan will recognize the established methods of animal immunizations. Furthermore, one skilled in the art realizes that the test antigens can be derived from organisms, subunits of proteins/antigens, killed or inactivated whole cells or lysates. Examples of potential vaccines to be used with this invention include, but are not limited to cancer vaccines, bacterial vaccines, viral vaccines or parasitic vaccines.

EXAMPLE 2

Determination of the Capability of the Rotavirus Enterotoxin NSP4 to Potentiate Mucosal Immune Response to Keyhole Limpet Hemocyanin (KLH)

NSP4 viral enterotoxin was demonstrated to modulate mucosal immune response to KLH. Balb/c mice were immunized intranasally at days 0 and 21 with 6, 10, or 20 µg of NSP4 proteins of simian (SA11, SEQ.ID.NO:24 or NSP4 aa 112-175, SEQ.ID.NO:22) or porcine (OSU, SEQ.ID.NO:25) origin, 10 µg of mutant LT (LT-R192G), or buffer. The antibody responses were evaluated using ELISAs to determine the total fecal IgA (µg/ml), KLH-specific fecal IgA (ng/ml), and KLH-specific serum IgG antibody titers.

The data show that 6 µg of simian SA11 NSP4 enterotoxin can act as an effective mucosal adjuvant when administered intranasally to mice with KLH as the test antigen. FIGS. 1 and 2 illustrate that NSP4 enhanced the specific serum IgG and fecal IgA immune response to KLH significantly (p<0.03, Mann Whitney U) compared to the immune response induced by KLH alone. KLH-specific serum IgG and fecal IgA were not detected in mice immunized with NSP4 alone. Although the NSP4 adjuvant activity with KLH was weaker than that of a nontoxic mutant of LT (LT-R192G), there is no evidence that NSP4 binds $G_{M1}$, making NSP4 a safer and more practical adjuvant candidate than CT and LT mutants.

EXAMPLE 3

Determination of the Capability of the Rotavirus Enterotoxin NSP4 to Potentiate Mucosal and Systemic Immune Responses to Non-Replicating Antigens NSP4 possess immunopotentiating activity with a broad variety of antigens. Non-replicating model antigen, ovalbumin (OVA), a particulate non-replicating candidate vaccine, rotavirus-like particles (RV-VLPs) (Ciarlet, et al., 1998, and O'Neal, et al., 1998), and an inactivated influenza A virus (Mbawuike, et al., 1990) are used in the presence or absence of NSP4 as the adjuvant. Rotaviruses are the major agents that cause severe gastroenteritis in children (Ciarlet, et al., 1998), and influenza A viruses cause a serious respiratory illness in both children and adults (Mbawuike, et al., 1990). RV-VLPs and influenza A antigens were chosen as test antigens because well established mouse models are available, both systemic and mucosal immunization routes are efficacious in both models, protection at two distinct mucosal surfaces (respiratory and intestinal tracts) can be tested and the test antigens are under vaccine development or are in use in humans (Ciarlet, et al., 1998, O'Neal, et al., 1998, Mbawuike , et al., 1990, Mbawuike, et al., 1993, and Ciarlet, et al., 2000).

One example to study the adjuvanticity of NSP4, but not limited to this example, is to use adult Balb/c mice (6 per group) immunized orally, intranasally or parenterally at days 0 and 21 with test antigens at sub-optimal antigen doses using the established protocols stated in example 1 (Ciarlet, et al., 1998, O'Neal, et al., 1998, Mbawuike, et al., 1990, Mbawuike, et al., 1993, Ciarlet, et al., 2000, and Ciarlet, et al., 1999b). The test antigens are administered in conjunction with increasing concentrations (5, 10, or 20 $\mu$g) of SA11 NSP4, PBS, or 10 $\mu$g of mutant LT (LT-R192G) or 20 $\mu$g of QS-21, as control adjuvants for mucosal or systemic routes of immunization, respectively. Already established specific IgG and IgA ELISAs, and neutralization (rotavirus) or hemagglutination-inhibition (influenza A) assays (Ciarlet, et al., 1998, O'Neal, et al., 1998, Mbawuike, et al., 1990, Mbawuike, et al., 1993, and Ciarlet, et al., 2000) are used to evaluate antibody responses to each combination of test antigens and adjuvants in serum and fecal samples.

EXAMPLE 4

Different Types of NSP4 and Potency

Based on amino acid sequence divergence (60–85%), there are 4 known genotypes of group A NSP4: A, B, C and D (Ciarlet, et al., 1999b). These NSP4s have been cloned and expressed in the baculovirus expression system (BES) using standard procedures well known in the art (Zhang, et al., 1998).

Briefly, NSP4 that was cloned into a vector was subcloned into the baculovirus transfer vector. Recombinant baculoviruses expressing NSP4 were generated and recombinant virus stocks were plaque purified. NSP4 was purified from Sf9 cells infected with the recombinant baculovirus. Infected cells were harvested and lysed with lysis buffer.

NSP4 was first semipurified by fast-performance liquid chromatography (FPLC) using a quaternary methylamine anion-exchange column. The NSP4-rich fractions were pooled for futher purification by using an agarose imunoaffinity column onto which rabbit immunoglobulin G (IgG) against SA11 NSP4 had been immobilized. NSP4 was eluted from the column and the eluate was then dialyzed and lyophilized.

The adjuvanticity of all NSP4 types is determined using the experimental design described in Example 3. The choice of test antigen, dose of NSP4, route of immunization, and control adjuvant tested is the regimen identified in Example 3 with the most enhanced immune response.

EXAMPLE 5

Challenge Studies Using the Most Potent NSP4 Adjuvant

The experimental design is the same as described in Example 3, except mice are challenged at a determined time point after vaccination. The optimal dose, type of NSP4, route of immunization, and control adjuvant are chosen based on results obtained in Example 4. Antibody responses are analyzed by ELISAs, and hemagglutination-inhibition or neutralization assays. Protective efficacy is evaluated by protection from rotavirus infection (reduction in virus shedding) or influenza A disease (reduction in mortality) (Ciarlet, et al., 1998, O'Neal, et al., 1998, Mbawuike, et al., 1990, Mbawuike, et al., 1993, and Ciarlet, et al., 2000).

EXAMPLE 6

Figure 2:
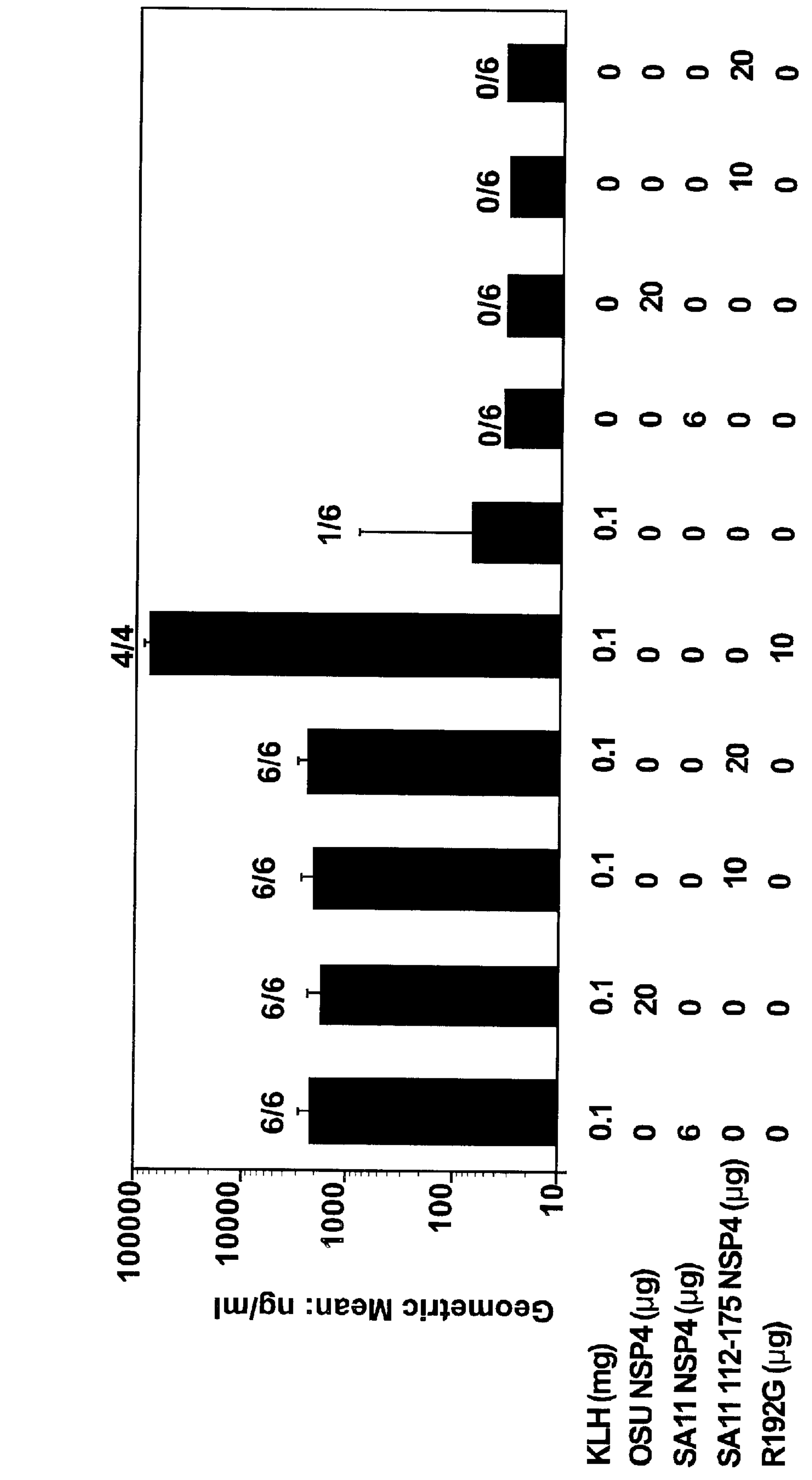
FIG. 2 shows the antibody responses evaluated by ELISAs of intestinal immunoglobulin (IgA) immune response to KLH administered intranasally in the presence or absence of rotavirus enterotoxin or LT.

Development of Nontoxic Derivatives of NSP4 which Retain Adjuvanticity and Identification of the Domain in NSP4 Responsible for Adjuvant Activity The region between amino acid residues 131 to 140 of the wild-type OSU NSP4 (type B) (SEQ.ID.NO: 25) is important in enterotoxicity because a single amino acid change at position 138 (P→S) renders the protein (OSU NSP4-P138S, SEQ.ID.NO:23) nondiarrheagenic in neonatal mice (Zhang, et al., 1998). Recently, a secreted non-glycosylated protease cleavage product of SA11 NSP4 aa 112-175 (SEQ.ID.NO:22) that retains enterotoxin function in mice has been cloned and produced in the baculovirus expression system. The data in FIGS. 1 and 2 show that 10 $\mu$g of SA11 NSP4 aa 112-175 retains similar (p=0.89, Mann Whitney U) adjuvant activity to that of the full-length SA11 NSP4 (SEQ.ID.NO: 24) when administered intranasally to Balb/c mice with KLH as the test antigen. SA11 NSP4 aa 112-175 enhanced the specific serum IgG and fecal IgA immune response to KLH significantly (p<0.02, Mann Whitney U) compared to the immune response induced by KLH alone. These data indicate that the adjuvant and enterotoxic domain in NSP4 are contained in the C-terminus of the protein. Additionally, expressed NSP4 aa 112-175 is more soluble than the glycosylated and hydrophobic full-length SA11 NSP4.

EXAMPLE 7

Adjuvant Activity of Rotavirus Fusion Proteins or Cross-Linked Proteins

Fusion proteins containing rotavirus enterotoxin or a derivative are fused to an antigen and prepared using standard methods well known in the art. In addition to fusion proteins, rotavirus enterotoxin or a derivative may be covalently coupled or cross-linked to antigens (Cryz et al., 1994, Liang et al., 1988, Czerkinsky, et al., 1989) using established protocols well known in the art.

The adjuvanticity of fusion proteins or cross-linked adjuvant or adjuvant peptides to an antigen is determined using the experimental design in Example 3.

REFERENCES

All patents and publications mentioned in the specification are indicative of the level of those skilled in the art to which the invention pertains. All patents and publications are herein incorporated by reference to the same extent as if each individual publication was specifically and individually indicated to be incorporated by reference.

Ball J M, Tian P, Zeng C Q-Y, Morris A P, Estes M K (1996) Age-dependent diarrhea induced by a rotaviral nonstructural glycoprotein. Science 272:101–104.

Cheng E, Cárdenas-Freytag L, Clements J (1999). The role of cAMP in mucosal adjuvanticity of *Escherichia coli* heat-labile enterotoxin (LT). Vaccine, 18:38–49.

Ciarlet M, Liprandi F, Conner M E, Estes M K (2000) Species specificity and interspecies relatedness of NSP4 genetic groups by comparative NSP4 sequence analyses of animal and human rotaviruses. Arch Virol. 145:371–383.

Ciarlet M, Conner M E (2000) Evaluation of rotavirus vaccines in small animal models. In: Desselberger U, Gray J (eds) Methods in Molecular Virology, vol. 34. Humana Press, New Jersey. pp.147–187.

Ciarlet M, Crawford S E, Barone C, Bertolotti-Ciarlet A, Estes M K, Conner M E (1998) Subunit rotavirus vaccine administered parenterally to rabbits induces active protective immunity. J Virol 72:9233–9246.

Cryz S J Jr, Wedgwood J, Lang A B, Ruedeberg A, Que J U, Furer E, Schaad U B (1994) Immunization of noncolonized cysTIC fibrosis patients against Pseudomonas aeruginosa. J Infect Dis. 169:1159–62.

Czerkinsky C. Russell M W, Lycke N, Lindblad M, Holmgren (1989) Oral administration of a streptococcal antigen coupled to cholera toxin B subunit evokes strong antibody responses in salivary glands and extramucosal tissues. J Infect Immun 57:1072–7.

Dong Y, Zeng C Q-Y, Ball J M, Estes M K, Morris A P (1997) The rotavirus enterotoxin NSP4 mobilizes intracellular calcium in human intestinal cells by stimulating phospholipase C mediated inositol 1,4,5-triphosphate production. Proc Natl Acad Sci USA 94:3960–3965.

Freytag L, Clements, J (1999) Bacterial toxins as mucosal adjuvants. Curr Top Microbiol Immunol 236:215–236.

Gradon J, Lutwick L (1999) Maintaining and enhancing vaccine immunogenicity. Infect Dis Clin North Am 13:39–60.

Levine M M, Kaper J B, Black R E, Clements M L (1983) New knowledge on pathogenesis of bacterial enteric infections as applied to vaccine development. Microbiol Rev 47:510–550.

Liang X P, Lamm M E, Nedrud J G (1988) Oral administration of cholera toxin-Sendai virus conjugate potentiates gut and respiratory immunity against Sendai virus. J Immunol 141:1495–501.

Lycke N, Karlsson U, Sjolander A, Magnusson K-E (1991) The adjuvant effect of cholera toxin is associated with an increased intestinal permeability for luminal antigens. Scand J Immunol 33:691–698.

Lycke N, Tsuji T, Holmgren J (1992) The adjuvant effect of *Vibrio cholerae* and *Escherichia coli* heatlabile enterotoxins is linked to their ADP-ribosyltransferase activity. Eur J Immunol 22:2277–2281.

Mbawuike I, Wyde P R (1993) Induction of CD8+ cytotoxic cells by immunization with killed influenza virus and effect of cholera toxin B subunit. Vaccine 11:1205–1213.

Mbawuike I, Wyde P R, Anderson P (1990) Enhancement of the protective efficacy of inactivated influenza A virus vaccine in aged mice by IL-2 liposomes. Vaccine 8:347–352.

Morris A P, Scott J K, Ball J M, Zeng, C Q-Y, O'Neal W K and Estes M K (1999) NSP4 elicits age-dependent diarrhea and Ca2-mediated I-influx into intestinal crypts of CF mice. American Physiological Society 277:G431–G444.

O'Neal C, Clements J D, Estes M K, Conner M E (1998) Rotavirus 2/6 virus-like particles administered intranasally with cholera toxin, *Escherichia coli* heat-labile toxin (LT), and LT-R192G induce protection from rotavirus challenge. J Virol 72:3390–3393.

Peterson J W, Finkelstein R A, Cantu J, Gessell D L, and Chopra, A K (1999) Cholera Toxin B Subunit Activates Arachidonic Acid Metabolism. Infection and Immunity 67:794–799.

Tian, P, Hu, Y., Schilling, W P, Lindsay, D A, Eiden, J and Estes M K (1994) The Nonstructural Glycoprotein of Rotavirus Affects Intracellular Calcium Levels. J. Virol 68:251–257.

Wu Y-Y, Nahm M H, Guo Y, Russell M W, Briles D E (1997) Intranasal immunization of mice with PspA (pneumococcal surface protein A) can prevent intranasal carriage, pulmonary infection, and sepsis with Streptococcus pneumoniae. J Infect Dis 175:839–846.

Xu-Amano J, Jackson R J, Fujihashi K, Kiyono H, Staats H F, McGhee JR (1994) Helper Th1 and Th2 cell responses following mucosal or systemic immunization with cholera toxin. Vaccine 12:903–911.

Xu-Amano J, Kiyono H, Jackson R J, Staats H F, Fujihashi K, Burrows P D, Elson C O, Pillai S. McGhee JR (1993) Helper T cell subsets for immunoglobulin A responses: oral immunization with tetanus toxoid and cholera toxin as adjuvant selectively induces Th2 cells in mucosal associated tissues. J Exp Med 178:1309–1320.

Yamamoto M, Vancott J L, Okahashi N, Marimanr M, Kiyono H, Fujihashi K, Jackson R J, Chatfield S N, Bluethmann H, McGhee JR (1996) The role of Th1 and Th2 cells for mucosal IgA responses. Ann NY Acad Sci 778:64–71.

Yamamoto S, Takeda Y, Yamamoto M, Kurazono H, Imaoka K, Yamamoto M, Fujihashi K, Noda M, Kiyono H, McGhee JR (1997b) Mutants in the ADP-ribosyltransferase cleft of cholera toxin lack diarrheagenicity but retain adjuvanticity. J Exp Med 185:1203–1210.

Zeng C Q-Y and Estes M K (1999) unpublished data.

Zhang M, Zeng C Q-Y, Dong Y, Ball J M, Saif L J, Morris A P, Estes M K (1998) Mutations in rotavirus nonstructural glycoprotein NSP4 are associated with altered virulence. J Virol 72:3666–3672.

Zhang M, Zeng C Q-Y, Scott J, Morris A, Estes M K (2000) Identification of secreted forms of the rotavirus enterotoxin NSP4. J. Virol. In press.

One skilled in the art readily appreciates that the present invention is well adapted to carry out the objectives and obtain the ends and advantages mentioned as well as those inherent therein. Methods, procedures and techniques described herein are presently representative of the preferred embodiments and are intended to be exemplary and are not intended as limitations of the scope. Changes therein and other uses will occur to those skilled in the art which are encompassed within the spirit of the invention or defined by the scope of the pending claims.

I claim:

1. A method of potentiating an immune response against an antigen in an animal comprising the step of administering to said animal a heterologous antigen and an adjuvant wherein said adjuvant is selected from the group consisting of an isolated rotavirus NSP4, NSP4 fragment aa 112-175, and NSP4 comprising one or more mutations in aa 1-111, wherein said adjuvant is present in an adjuvanting effective amount to potentiate the immune response against the heterologous antigen.

2. The method of claim 1 wherein said antigen and said adjuvant are administered to a mucosal surface of said animal.

3. The method of claim 2 wherein said mucosal surface is selected from the group consisting of intranasal surface, oral surface, rectal surface and genitourinary tract surface.

4. The method of claim 1 wherein said antigen and said adjuvant are administered parenterally to said animal.

5. The method of claim 4 wherein said administration is intraperitoneal, intravenous, intradermal, dermoabsorption, intramuscular or subcutaneous.

6. The method of claim 1 wherein said immune response is systemic.

7. The method of claim 1 wherein said immune response is mucosal.

8. The method of claim 1 wherein said antigen is selected from a group consisting of rotavirus-like particles and influenza A virus.

9. The method of claim 8 wherein said antigen is an inactivated influenza A virus.

10. The method of claim 1 wherein said antigen and said adjuvant are co-administered.

11. The method of claim 1 wherein the animal is a mammal.

12. The method of claim 1 wherein the animal is an avian species.

13. The method of claim 1 wherein the animal is a human.

14. A method of potentiating an immune response against influenza A virus in an animal comprising the steps of administering to a mucosal surface of said animal a heterologous inactivated influenza A virus antigen, and administering an adjuvant wherein said adjuvant is selected from the group consisting of an isolated rotavirus NSP4, NSP4 fragment aa 112-175, and NSP4 comprising one or more mutations in aa 1-111, wherein said adjuvant is present in an adjuvanting effective amount to potentiate the immune response against the heterologous antigen.

15. A method of potentiating an immune response to heterologous rotavirus-like particles in an animal comprising the steps of administering to the mucosal surface of said animal rotavirus-like particles, and administering an adjuvant wherein said adjuvant is selected from the group consisting of an isolated rotavirus NSP4, NSP4 fragment aa 112-175, and NSP4 comprising one or more mutations in aa aa 1-111, wherein said adjuvant is present in an adjuvanting effective amount to potentiate the immune response against the rotavirus-like particles.

16. The method of claim 5, wherein the administration is intramuscular.

17. The method of claim 3, wherein the mucosal surface is intranasal.

* * * * *

SEQUENCE LISTING

<160> NUMBER OF SEQ ID NOS: 25

<210> SEQ ID NO 1
<211> LENGTH: 751
<212> TYPE: DNA
<213> ORGANISM: Rotavirus strain ALA

<400> SEQUENCE: 1

```
ggcttttaaa agttctgttc cgagagagcg cgtgcggaaa gatggataaa cttaccgacc     60

tcaattacac attgagcgta atcactttaa tgaatagtac attgcatgca atattggaag    120

atccagggat ggcgtatttc ccatacatag catctgtgtt gactgttctg ttcactttac    180

ataaagcatc aattccaaca atgaaaattg cgttaaaaac atctagatgt tcctacaaag    240

ttattaaata ttgcattgta accatattta atacattgtt gaaattagct ggatataaag    300

aacaaataac tactaaagat gaaattgaaa aacagatgga tagagtaatc agagaaatga    360

gacgtcagtt ggaaatgatt gataaattga caactcgtga aattgaacag gtagaactac    420

taagacgtat atatgacaga ttaacggtac gaaagactga tgagatagat atgtcgaagg    480

agatcaatca gaaaaatata cgaacgctag atgaatggga gaatggaaaa aatccatatg    540

aaccaagcga agtgaccgca tcattgtgag aggttggact gccgtcgact gtctctggaa    600

gcggcggagt ccttcacagt aagtcccatc ggacctgatg actggctgag aagccacagt    660

cagtcatatc gcgtgtggct caagccttaa tcccgtttaa ccaatccggt gagcgccgga    720

cgttaatgga aggaatggtc ttagtgtgac c                                   751
```

<210> SEQ ID NO 2
<211> LENGTH: 751
<212> TYPE: DNA
<213> ORGANISM: Lapine rotavirus strain C-11

<400> SEQUENCE: 2

```
ggcttttaaa agttctgttc cgagagagcg cgtgcggaaa gatggataaa cttaccgacc     60

tcaattacac attgagcgtg atcactttaa tgaatagtac attgcataca atattggaag    120

atccagggat ggcgtatttc ccatacatag catctgtgtt gactgttctg ttcactttgc    180

ataaagcatc aattccaaca atgaaaattg cgttaaaaac atctagctgt tcctacaaag    240

ttattaaata ttgtcttgtt actatattta atacattgcc taaattagct ggatataaag    300

aacaaataac tactaaacgt gaaattgaaa aacagatgga tagagttatc agagaaatga    360

gacgtcagtt agaaatgatt gataaattga caactcgtga aattgaacag gtagaactac    420

taagacgtat atatgacaaa ttaacggtac gaaagactga tgagataggt atgttgaagg    480

agatcaatca gaaaaatata cggacgctag atgaatggga gaatggaaag aatccatacg    540

aaccaagcaa agtgaccgca tcattgtgag aggttggact gccgtcgact gtcctggaag    600

cggcggagtc cttcacagta agtcccatcg gacctgatga ctggctgaga agccacagtc    660

atatcatatc gcgtgtggct caagccttaa tcccgtttaa ccaatccggt gagcgccgga    720

cgttaatgga aggaatggtc ttagtgtgac c                                   751
```

<210> SEQ ID NO 3
<211> LENGTH: 751
<212> TYPE: DNA
<213> ORGANISM: Lapine rotavirus strain R-2

<400> SEQUENCE: 3

-continued

```
ggcttttaaa agttctgttc cgagagagcg cgtgcggaaa gatggaaaag cttaccgacc     60
tcaactatac attgaatgtg atcactttat tgaacagtac attgcataca atattggagg    120
atccagggat ggcgtacttt ccttacattg catctgtcct aacagtttta ttcacattac    180
acaaagcgtc gattccaacg atgaaaattg ccttaagaac atcaaaatgt tcctataaag    240
tgataaagta ttgtattgta acaattttca atacgctact aaagttagcc ggctataaag    300
aacagattac tactaaagaa tggattgaaa aacagttgga caaagtaata aaagaaatga    360
gacgtcagct agaaatgata gataaattga caactcgaga aattgaacag gtagagctac    420
taaaacgtat atacgacaaa ctaatgatac gaaagactga tgaaatagat atgacgaagg    480
agatcaatca aaaaaatgta aaaacgctag atgaatggga gaatgggaag aatccatatg    540
aatcaaaaga agtgactgca gcaatgtaag aggttgggct gccgtcgact gtcttcggaa    600
gcggcggagt tcttcacagt aagttccatc ggacctgatg agtggctgag aagccacagt    660
cagtcatatc gcgtgtggct caagccttaa tcccgtttaa ccaatccggt gagcgccgga    720
cgttaatgga aggaagggtc ttagtgtgac c                                   751
```

<210> SEQ ID NO 4
<211> LENGTH: 751
<212> TYPE: DNA
<213> ORGANISM: Lapine rotavirus strain BAP-2

<400> SEQUENCE: 4

```
ggcttttaaa agttctgttc cgagagagcg cgtgcggaaa gatggataaa cttaccgacc     60
tcaattacac attgagcgta atcactttaa tgaatagtac attgcatgca atattggaag    120
atccagggat ggcgtatttc ccatacatag catctgtgtt gactgtactg ttcactttac    180
ataaagcatc aattccaaca atgaaaattg cgttaaaaac atctagatgt tcctacaaag    240
ttattaaata ttgcattgta accatattta atacattgtt gaaattagct ggatataaag    300
aacaaataac tactaaagat gaaattgaaa gacagatgga cagagtagtc cgagaaatga    360
gacgtcagtt ggaaatgatt gataaattga caacacgtga aattgaacag gtagaactac    420
taagacgtat atacgacaga ctaacggtgc gaaagactga tgagatagat atgtcgaagg    480
agatcaatca gaaaaatata cggacgttag atgaatggga gaatggaaaa aatccatatg    540
aaccaagcga ggtgaccgca tcattgtgag aggttggact gccgtcgact gtccctggaa    600
gcggcggagt cctttacagt aagtcccatc ggacctgatg actggctgag aagccacagt    660
cagtcatatc gcgtgtggct caagccttaa tcccgcttaa ccaatccggt gagcgccgga    720
cgttaatgga aggaatggtc ttagtgtgac c                                   751
```

<210> SEQ ID NO 5
<211> LENGTH: 751
<212> TYPE: DNA
<213> ORGANISM: Lapine rotavirus strain BAP (wildtype)

<400> SEQUENCE: 5

```
ggcttttaaa agttctgttc cgagagagcg cgtgcggaaa gatggataaa cttaccgacc     60
tcaattacac attgagcgta atcactttaa tgaatagtac attgcatgca atattggaag    120
atccagggat ggcgtatttc ccatacatag catctgtgtt gactgtactg ttcactttac    180
ataaagcatc aattccaaca atgaaaattg cgttaaaaac atctagatgt tcctacaaag    240
ttattaaata ttgcattgta accatattta atacattgtt gaaattagct ggatataaag    300
```

-continued

```
aacaaataac tactaaagat gaaattgaaa agcagatgga cagagtaatc cgagaaatga    360

gacgtcagtt ggaaatgatt gataaattga caactcgtga aattgaacag gtagaactac    420

taagaagaat atacgacaga ctaacggtac gtaagactga tgagatagat atgtcgaagg    480

aaatcaatca gaaaaatata cggacgttag atgaatggga gaatggaaaa aatccatatg    540

aaccaagcga ggtgaccgca tcattgtgag aggttggact gccgtcgact gtccctggaa    600

gcggcggagt ccttcacagt aagtcccatc ggacctgatg actggctgag aagccacagt    660

cagtcatatc gcgtgtggct caagccttaa tcccgtttaa ccaatccggt gagcgccgga    720

cgttaatgga aggaatggtc ttagtgtgac c                                   751
```

<210> SEQ ID NO 6
<211> LENGTH: 750
<212> TYPE: DNA
<213> ORGANISM: Porcine rotavirus strain A253

<400> SEQUENCE: 6

```
ggcttttaaa agttctattt cgagagagcg cgtgcggaaa gatggataag cttgcagacc     60

ttaattatac tttgagcgtt atcactttaa tgaatgatac actacactct ataattcaag    120

atccagggat ggcgtacttc ccatatattg catctgtact gactgtatta tttactctac    180

ataaggcatc aattcccaca atgaaaattg cgttaaaaac gtcaaagtgt tcgtacaaag    240

taattaagta ttgcatggtt acaatcatta atactcttct gaagttggct ggttacaagg    300

aacaggttac tactaaggac gaaattgaac aacagatgga tagaattgta aaagagatga    360

gacgtcaact ggaaatgatt gataaattga ctactcgtga aattgaacag gtagaattac    420

ttaaacgtat acacgataaa ttggtagtta gacctgtaga cgttatagac atgtcgaaag    480

aatttaacca gaaaaatatt agaacgctag acgaatggga aagtgggaaa aatccatacg    540

aaccctcgga agttactgcg tctatgtgag aggttgagtt gccgtcgtct gtcttcggaa    600

gcggcggaac tcttcaccgc aagccccatt ggacacgatg gtttactgac aaaccccagt    660

caatcatttc gcgtgtagca catccctaat cccgaataac caatccagcg aatgttggac    720

gttaatggaa ggaatggtct taatgtgacc                                     750
```

<210> SEQ ID NO 7
<211> LENGTH: 750
<212> TYPE: DNA
<213> ORGANISM: Porcine rotavirus strain A131

<400> SEQUENCE: 7

```
ggcttttaaa agttctgttt cgagagagcg cgtgcggaaa gatggataag cttgcagacc     60

ttaattacac tttgagcgtt attactttaa tgaatgacac actacattct attattcaag    120

atccagggat ggcgatcttc ccatatatag catctgtact gactgtatta tttactctac    180

ataaggcatc aatacccaca atgaaaattg cgttaaaaac gtcaaagtgt tcgtataaag    240

taataaagta ctgcattgtt acaattatca atactcttct gaaattggct ggttacaagg    300

aacaggttac tacaaaggat gaaattgaac aacagatgga cagaatcatt aaagagatga    360

gacgtcaact ggaaatgata gataagttga ctactcgtga aattgaacag gtagaattac    420

ttaagcgtat tcatgataag ttggttgtaa ggccagtaga cgttattgac atgtcgaaag    480

aatttaatca gaagaatata cgaacgcttg acgaatggga aagtggaaaa aatccatacg    540

aaccgtcgga agtaactgca tctatgtgag aggttgagtt accctcgtct gtatttggga    600

gcggcgggac tcttcatcgc aaaccacatt ggacacgatg gtttactgac aaaccccagt    660
```

-continued caatcatatc gcgtgtagca cagccataat cccgtataac aaatcctgcg aatgttggac 720
gttaatggaa ggaatggtct taatgtgacc 750

<210> SEQ ID NO 8
<211> LENGTH: 750
<212> TYPE: DNA
<213> ORGANISM: Porcine rotavirus strain A411

<400> SEQUENCE: 8
ggcttttaaa agttctgttc cgagagagcg cgtgcggaaa gatggataag cttgacgatc 60
ttaattatac tttgagcgtc atcactttaa tgaatgacac actacattct ataattcaag 120
atccaggaat ggcgtacttc ccatacatag catctgtact gactgtttta tttactctac 180
ataaggcatc aattcccaca atgaaaattg cgttaagaac gtcaaagtgt tcgtataaag 240
taataaaata ctgcattgtt acaattttta atactcttct gaaattggct ggttacaaag 300
aacaggttac tactaaagac gaaattgaac aacagatgga cagaattatc aaagagatga 360
gacgtcaact ggaaatgatt gacaaattga ctactcgtga aattgaacag gtagaattac 420
ttaaacgtat tcacgataaa ctggttgcaa ggtcagttga cgttatagac atgtcgaaag 480
aatttaatca gaaaaatata agaacgctag atgaatggga aagtggaaaa aatccctacg 540
aaccgtcgga agtaactgca tctatgtgag aggttgagtt gccgtcatca gtctttggga 600
gcggcggaac tcttcatcgc aagccccatt ggacccgatg gttgactgag aagccacagt 660
caatcatttc tcgtgtagca cagccctaat cccgattaac caatccagcg aatgttggac 720
gttaatggaa ggaatggtct taatgtgacc 750

<210> SEQ ID NO 9
<211> LENGTH: 675
<212> TYPE: DNA
<213> ORGANISM: Porcine rotavirus strain A34

<400> SEQUENCE: 9
gatggataag cttgccgacc tcaactacac attgagtgta atcactttaa tgaatgatac 60
gttacactct attattcaag atccaggaat ggcgtatttt ccatatatcg catctgttct 120
aactgtttta tttactctac ataaagcatc aattccaacg atgaaaatag cattaagaac 180
gtcaaaatgt tcatacaaag taattaaata ttgtatggtt acgatcatta atactcttct 240
aaagttggct ggttataaag aacaggttac taccaaggat gaaatcgaac aacagatgga 300
cagaattgtt aaagagatga gacgtcaact ggagatgatt gacaaattga caactcgtga 360
aattgaacag gtcgaattac ttaagcgtat acatgataaa ttagttacta gaccagttga 420
tgctatagac atgtcgaaag aatttaatca gaagaatatc agaacgctag atgaatggga 480
aagcggaaaa aatccatatg aaccatcaga agtgactgca tctatgtgag aggttgagtt 540
gccgtcgtct gtcttcggaa gcggcggaac tcttcaccgc aagccccatt ggacctgatg 600
gttgactgag aagccacagt caatcatatc gcgtgtggct cagccttaat cccgtttaac 660
caatccagcg aatgt 675

<210> SEQ ID NO 10
<211> LENGTH: 751
<212> TYPE: DNA
<213> ORGANISM: Equine rotavirus strain H-2

<400> SEQUENCE: 10

-continued

```
ggcttttaaa agttctgttc cgagagagcg cgtgcggaaa gatggataag cttaccgacc     60
tcaactatac attgaatgtg atcactttat tgaacagtac attgcataca atattggagg    120
atccagggat ggcgtacttt ccttacattg catctgtcct aacagtttta ttcacattac    180
acaaagcgtc gattccaacg atgaaaattg ccttaagaac atcaaaatgt tcgtataaag    240
tgataaagta ttgtattgta acaattttca atacgctact aaagttagca ggctataaag    300
aacagattac tactaaagat gaaatagaaa aacaaatgga tagagtagtt aaagaaatga    360
gacgtcattt agagatgatt gataaattga ctacacgtga aattgaacaa gtagaattac    420
ttaaacgtat ttatgataaa ctgatgatac gggcaacaga cgaaatagat atgacgaaag    480
aaatcaatca aaagaacgtg aaaacgctag aagaatggga aaatggaaag aatccttatg    540
aatcaaaaga agtgactgca gcaatgtaag aggttgagct gccgtcgact atcttcggaa    600
gcggcggagt tctttacagt aagctccatc agacctgatg gctggctgag aagccacagt    660
cagccatatc gcgtgtggct caagccttaa tcccgtttaa ccaatccggt cagtaccgga    720
cgttaatgga aggagtggtc ttagtgtgaa g                                   751
```

<210> SEQ ID NO 11
<211> LENGTH: 751
<212> TYPE: DNA
<213> ORGANISM: Equine rotavirus strain FI-23

<400> SEQUENCE: 11

```
ggcttttaaa agttctgttc cgagagagcg cgtgcggaaa gatggataag cttaccgacc     60
ttaattatac attgaatgta attactctat tgaacagtac attgcataca attttagagg    120
atccagggat ggcgtatttc ccttacattg catctgtact aacagtatta ttcacattac    180
acaaagcgtc gattccaacg atgaagattg ccttaagaac atcaaaatgt tcgtacaagg    240
tgattaagta ttgtatagtt acaattttca atacgctact aaagttagca ggctataagg    300
aacagattac tactaaggac gaaatagaaa aacaaatgga tagagttgtt aaagaaatga    360
ggcgtcacct agagatgata gataagttga ctacacgtga aatagagcaa gttgaattac    420
ttaaacgtat atacgataag ctgatggcac gagcaacaga tgaaattgat atgactaaag    480
aaataaatca gaagaacgtg aaaacgttag aagaatggga aaatggaaag aatccttacg    540
aatcaaaacg aatgactgca gcaatgtaag aggttgaact gccgtcgact atctttggaa    600
gcgggggggt actatatagt aagctccatc agacctaata gctggctgag aagccacagt    660
cagcaattta aaaagtggct caagccttaa ttcccttcaa ccaatccggt cagtaccgga    720
cgttaatgga aggagtggtc ttagtgtgaa g                                   751
```

<210> SEQ ID NO 12
<211> LENGTH: 751
<212> TYPE: DNA
<213> ORGANISM: Equine rotavirus strain FI-14

<400> SEQUENCE: 12

```
ggcttttaaa agttctgttc cgagagagcg cgtgcggaaa gatggataaa ctaaccgacc     60
tcaactatac attgaacgta atcactttaa ttaacagcac attgcataca attttagagg    120
atcccggaat ggcgtatttc ccttacattg catctgtatt aacagtatta ttcacattac    180
acaaggcatc gataccaacg atgaagatag ccttgaaaac atcaaagtgt tcgtataaag    240
tagtaaaata ctgtatagtt acaattttta atacgctact aaaattagca ggctacaaag    300
aacaaataac tactaaagat gaaattgaga agcaaatgga cagagtaatt aaagaaatga    360
```

-continued

```
gacgtcattt agagatgata gacaagttga caactcgtga gatagagcaa gttgaactac    420

ttaagcgtat atacgataag ctaatgattc gggctacgga cgaaattgat atgtcgaaag    480

aaattaacca aaagaacgta agaacgttag aagaatggga aaacggaaag aatccttatg    540

aatcaaaaga agttactgca gcaatgtaag aggttgagct gccgtcgact atcttcggaa    600

gcggcggagt attttacagt aagctccacc aaacctgatg gctggcagaa aaaccccatt    660

cagcaatttc gcgtgtggct cataacttaa ttccgttcaa tcactccggt cagtaccgga    720

cgttaatgga aggagtggtc ttagtgtgaa g                                   751
```

<210> SEQ ID NO 13
<211> LENGTH: 751
<212> TYPE: DNA
<213> ORGANISM: Bovine rotavirus strain BRV033

<400> SEQUENCE: 13

```
ggctttaaaa agttctgttc cgagagagtg tgtgcgggaa gatggagaag cttaccgacc     60

tcaactacac atcgagtgtt atcactctaa tgaacaacac attgcatacg attcttgagg    120

accccggaat ggcgtacttc ccatacattg catctgtcct aacagttttg tttacgttgc    180

acaaggcatc tatacctaca atgaagatag cactgaaaac gtccaagtgt tcatacaaag    240

tagtaaaata ctgtatagta acgatattca atacgttgtt gaaattggca ggttacaaag    300

aacagataac tactaaagat gagatagaaa agcaaatgga cagggttgtt aaagagatga    360

gacgtcagtt tgaaatgatt gataagttga ctacacgtga aatagagcag gtagagttgc    420

taaagcgcat acacgacaag ttgatggttc gagcaacaga tgagattgat atgacgaagg    480

aaataaacca aaagaacgta agaacgctag aagaatggga aaatggaaaa aatccttatg    540

aacccaagga ggtgactgca gcgatgtaag aggttgagct gccctcgact gtcttcggaa    600

gcggcggagt tcttcacagt aagccacatc ggacatgatg acttactgaa aagccccagt    660

cagtcatttc ccgagtggct taagccttaa tccccttcaa ccattcaggt cagcaccgga    720

cgttaatgga gggaacggtc ttaatgtgac a                                   751
```

<210> SEQ ID NO 14
<211> LENGTH: 751
<212> TYPE: DNA
<213> ORGANISM: Bovine rotavirus strain B223

<400> SEQUENCE: 14

```
ggctttaaaa agttctgttc cgagagagtg tgtgcgggaa gatggaaaag ctaaccgacc     60

tcaactatac attgagtgtt atcactctaa tgaactccac attgcatacg attcttgagg    120

accccgggat ggcgtacttc ccatatattg catcagtttt aacagtatta ttcacgttgc    180

acaaggcatc tatacccaca atgaagattg ctctaaagac gtccaagtgt tcatacaaag    240

tagtaaaata ttgcattgtt acgattttca atacgttgtt gaaattggct gggtacaaag    300

aacagataac tactaaagat gagatagaga aacagatgga aagggtagta aaggaaatga    360

gacgtcactt caaaatgata gacaaattga caactcgtga aattgagcag gtaggattgc    420

taaagcgcat tcacgacaag ttggatatac gggctgttga tgaaatagac atgacgaaag    480

aaattaacca gaaaaacgtt agaacgctag aagaatggga gtggggaaaa aatccctatg    540

aacccaaaga agttactgct gcaatgtaag aggttgagct accttcgaca gtattcggaa    600

gcgggggggt actacacagt aagcctcaac ggttatgttg actaactgag aaacctcaat    660
```

-continued

```
cagtcatttc cagagttttt taagccttaa tccccttcaa ccattcaggt cagcaccgga    720

cgttaatgga aggaacggtc ttaatgtgac a                                   751
```

<210> SEQ ID NO 15
<211> LENGTH: 750
<212> TYPE: DNA
<213> ORGANISM: Canine rotavirus strain CU-1

<400> SEQUENCE: 15

```
ggcttttaaa agttctgttc cgagaaagcg catgcggaaa gatggagaag cttgcagacc     60

tcaactatac cctgagtgta atcacgctaa tgaatgatac tttgcacact attatggagg    120

atcccggaat ggcatacttc ccatatattg catctgttct aactgtacta tttacattac    180

ataaggcatc aatcccaacc atgaaaatcg cacttaaaac atcaagatgt tcatacaagg    240

ttatcaagta ctgcatagta tcagtattta acactctatt gaagttggct ggatacaaag    300

agcagataac tactaaagat gaaatagaaa aacaaatgga cagagttgtt aaagaaatga    360

ggcgtcagct ggaaatgatt gataaactaa ccacaaggga gatagaacag gttgaacttc    420

ttaaacgaat acacgatatg ttaattgcaa agcccgtaga caagatagat atgtcgcaag    480

agttcaacca aaagcatttc aaaacactaa acgagtgggc agagggtgaa aatccatacg    540

aaccgagaga agtaactgca tctttatgag aggttgaact gccgtcttcg gtatgcggga    600

gcggaggagt aataaacaga aaatctcatc gaacttgatg aatggtagag aaacctcatt    660

cagtaatttc gcgggtgact tagtcttatt cacgttttac cattccagcc agtgctggac    720

gttaatggaa ggaatggtct taatgtgacc                                     750
```

<210> SEQ ID NO 16
<211> LENGTH: 750
<212> TYPE: DNA
<213> ORGANISM: Porcine rotavirus A

<400> SEQUENCE: 16

```
ggcttttaaa agttctgttc cgagagagcg cgtgcggaaa gatggataag cttgccgacc     60

tcaattacac attgagcgta atcactttaa tgaatgacac actacactct attattcaag    120

atccaggaat ggcgtatttt ccatatattg catctgttct gactgtttta tttactctac    180

ataaagcatc aattccaaca atgaaaatag cgttaaaaac gtcaaagtgt tcgtacaaag    240

taattaaata ttgcatggtt acaatcatta atactcttct gaagttggct ggttataaag    300

aacaggttac tactaaggat gaaattgaac aacagatgga cagaattatt aaagagatga    360

gacgtcaact ggaaatgatt gacaaattga cgactcgtga aattgaacag gttgaattac    420

ttaaacgtat acatgacaaa ttagctgcta gatcagttga cgctatagat atgtcgaaag    480

aatttaatca gaaaaatatt cgaacgctag atgaatggga aagtggaaaa aatccatatg    540

aaccgtcgga agtaactgcg tctatgtgag aggttgagtt gccgtcgtct gtcttcggaa    600

gcggcggaac tcttcaccgc aagccccatt ggacccgatg gttgactgag aagccacagt    660

caatcatatc gcgtgtggct cagccttaat cccgtttaac caatccagcg aatgttggac    720

gttaatggaa ggaatggtct taatgtgacc                                     750
```

<210> SEQ ID NO 17
<211> LENGTH: 528
<212> TYPE: DNA
<213> ORGANISM: Simian 11 rotavirus (strain SA11)

<400> SEQUENCE: 17

-continued atggaaaagc ttaccgacct caattataca ttgagtgtaa tcactctaat gaacaataca 60
ttgcacacaa tacttgagga tccaggaatg gcgtattttc cttatatagc atctgtctta 120
acagttttgt ttgcgctaca taaagcatcc attccaacaa tgaaaattgc attgaaaacg 180
tcaaaatgtt catataaagt ggtgaaatat tgtattgtaa caatttttaa tacgttgtta 240
aaattggcag gttataaaga gcagataact actaaagatg agatagaaaa gcaaatggac 300
agagtagtca aagaaatgag acgccagcta gaaatgattg acaaattgac tacacgtgaa 360
attgaacaag tagagttgct taaacgcatt tacgataaat tgacggtgca aacgacaggc 420
gaaatagata tgacaaaaga gatcaatcaa aaaaacgtga gaacgctaga agaatgggaa 480
agtggaaaaa atccttatga accaagagaa gtgactgcag caatgtaa 528

<210> SEQ ID NO 18
<211> LENGTH: 750
<212> TYPE: DNA
<213> ORGANISM: IDIR agent

<400> SEQUENCE: 18
ggcaaaataa aacccaaaga tgactgagaa taacgagatg caacaactat tcgtacaagc 60
agcgtatgaa gaaatcctaa agttagctga cagcgttgat catgaacaaa tacgcgagtc 120
catttcgaac tcatcgccac aaaaattgtt gactggtgcg ctactaacag tgacggctct 180
atttacaaca ttgatggtca gaaagaaagg aactcaattt ctaattcaaa aatttcagtc 240
aaatgtggtt catctgtcag aaatgttagt ttggaaagca agtcaaacag ttaaacaact 300
atgtgatgaa gtacttaatc aacatgaggt gctgcagaaa ttgcagtgtc tggatcaact 360
atgtgaagat gtaaggaaac tgagatataa cgtagaacac attaaaggtt tggatatttc 420
aaatgaattg ataagtttaa ccgaacgtaa aatggctgat atagacggaa gaatacgaga 480
tgttgagcgt tcatgcgata ggaagatcag agactatgat tggaaactag cagcactaac 540
ggcaaaccca gttcaccaaa ttgcagcgca cgtggacatg ataagtcaac acgaagaaaa 600
tgaggctgaa gcacaagata tccaacaaca cgtaaacaaa caagcaagag taaaaatgtc 660
atctagaagg ctttaacgat ccgtgggata gctaggaggc gtaaactctg tggttgtccc 720
tccccatcag atcaaacgag ataaaaaccc 750

<210> SEQ ID NO 19
<211> LENGTH: 613
<212> TYPE: DNA
<213> ORGANISM: Human rotavirus C

<400> SEQUENCE: 19
ggctttaaat ttttcagatc actttgctct acgaagtaat ggatttcatc aatcaaactt 60
tgttctcaaa gtatactgaa agtaatgtag atacaattcc ttatcttttg ggtcttattc 120
ttgcattaac taatggatca agaatactta gattcattaa ctcattcata atcatatgta 180
agcacatagt gactacgtct aaatcagcta ttgacaaaat gagaaaaatt aataattcgg 240
aacataacac aaagaatgcg catgaagaat atgaagaggt aatgaagcag ataagagaaa 300
tgcgtattca tatgactgca ttgtttaata gtttacatga tgataatgtt aaatggagaa 360
tgagtgaatc tattcgcaga gaaaagaaac atgaaatgaa gatgagtgat aatagaaatg 420
aattcaaaca ttcacataat gatacaaata tatgtgaaaa atctggatta gagacggaag 480
tttgtctatg aaatccctgc gcttcctgct ggtgaacgga cgccatcccg ttcatttcta 540

-continued

```
gcgagtagag aaaaacattg tacccgaaac gctgagttga ggatcaatgt agatatgaaa    600

aattcatgtg gct                                                       613


<210> SEQ ID NO 20
<211> LENGTH: 613
<212> TYPE: DNA
<213> ORGANISM: Human rotavirus C strain: Ehime 9301

<400> SEQUENCE: 20

ggctttaaat ttttcagatc actttgctct acgaagtaat ggatttcatc aatcaaactt     60

tgttctcaaa gtatactgaa agttatgtag atacaattcc ttatcttttg ggtcttattc    120

ttgcattaac taatggatca agagtactta gatttattaa ctcattcatc accatatgta    180

agcatatagt gattacgtct aaatcagcca ttgacaaaat gagaaaaatt aataattcgg    240

aacataacac aacgaatgcg catgaagaat atgaagaggt aatgaagcag ataagagaaa    300

tgcgtattca tatgactgca ttgtttaata gtttacatga tgataatgtt aaatggagaa    360

tgagcgaatc tattcgtcga gaaaagaaac atgaaatgaa gatgagtaat aatagaaatg    420

aattcaaaca ttcacataat gatacaaata tatgtgaaaa atctggatta gagacggaag    480

tttgtctatg aaattcctgc gcttcctgct ggtgaacgga cgccatcccg ttcatttcta    540

gcgagtagag aaaaacattg tacccgaaac gctgagttga ggatcaatgt agatatgaaa    600

aattcatgag gct                                                       613


<210> SEQ ID NO 21
<211> LENGTH: 719
<212> TYPE: DNA
<213> ORGANISM: Bovine rotavirus strain Shintoku

<400> SEQUENCE: 21

ggctttaaaa attgcgacaa tgtccgattt cggaattaat cttgatgcca tttgcgacaa     60

tgtcagaaga aattcatcaa attcaagtat caaatctcaa gtatcaaatc ggagttcacg    120

aaagatggat tttgttgatg aagatgagtt gagcacgtac ttcaattcaa aaacatccgt    180

gacacaatca gattcttgtt caaatgatct aaatgtgaaa cattcaatta tagcagaagc    240

tgtggtatgt gacgaatctg cgcatgtgtc tgcggatgcg gttcaagaaa aggatgtggt    300

tgttccaaaa atggatgaaa gtgttatgaa gtggatgatg gacagtcatg atggaatatg    360

tgtgaatgga ggtctgaact tttcaaaatt aaaaaataaa agtaatgaac atgaaactaa    420

agtaacgtca gaaacaaatg tatcagctca cgtttcagca ggaatcaatt cacaattggg    480

gatgttcaac ccaattcagc acaaaataaa gaaagaggct ataccagaaa tgtttgaaga    540

tgaagataca gatgaatgta cttgtagaaa ttgcccatat aaagaaaaat atcttaaact    600

ccgaaaaaaa ctgaaaaatg tgttagtcga tatcataact gaaatgtagt cgagtacttg    660

cccgtactgc atcaggtgac tggaatcggc attgagggga tccccaaccc gatctgtgg     719


<210> SEQ ID NO 22
<211> LENGTH: 64
<212> TYPE: PRT
<213> ORGANISM: Simian strain SA11

<400> SEQUENCE: 22

Met Ile Asp Lys Leu Thr Thr Arg Glu Ile Glu Gln Val Glu Leu Leu
1               5                   10                  15

Lys Arg Ile Tyr Asp Lys Leu Thr Val Gln Thr Thr Gly Glu Ile Asp
            20                  25                  30
```

-continued

Met Thr Lys Glu Ile Asn Gln Lys Asn Val Arg Thr Leu Glu Glu Trp
35 40 45

Glu Ser Gly Lys Asn Pro Tyr Glu Pro Arg Glu Val Thr Ala Ala Met
50 55 60

<210> SEQ ID NO 23
<211> LENGTH: 175
<212> TYPE: PRT
<213> ORGANISM: Porcine

<400> SEQUENCE: 23

Met Asp Lys Leu Ala Asp Leu Asn Tyr Thr Leu Ser Val Ile Thr Leu
1 5 10 15

Met Asn Asp Thr Leu His Ser Ile Ile Gln Asp Pro Gly Met Ala Tyr
20 25 30

Phe Pro Tyr Ile Ala Ser Val Leu Thr Val Leu Phe Thr Leu His Lys
35 40 45

Ala Ser Ile Pro Thr Met Lys Ile Ala Leu Lys Thr Ser Lys Cys Ser
50 55 60

Tyr Lys Val Ile Lys Tyr Cys Met Val Thr Ile Ile Asn Thr Leu Leu
65 70 75 80

Lys Leu Ala Gly Tyr Lys Glu Gln Val Thr Thr Lys Asp Glu Ile Glu
85 90 95

Gln Gln Met Asp Arg Ile Ile Lys Glu Met Arg Arg Gln Leu Glu Met
100 105 110

Ile Asp Lys Leu Thr Thr Arg Glu Ile Glu Gln Val Glu Leu Leu Lys
115 120 125

Arg Ile His Asp Lys Leu Ala Ala Arg Pro Val Asp Ala Ile Asp Met
130 135 140

Ser Lys Glu Phe Asn Gln Lys Asn Ile Arg Thr Leu Asp Glu Trp Glu
145 150 155 160

Ser Gly Lys Asn Pro Tyr Glu Pro Ser Glu Val Thr Ala Ser Met
165 170 175

<210> SEQ ID NO 24
<211> LENGTH: 175
<212> TYPE: PRT
<213> ORGANISM: Simian 11 rotavirus (strain SA11)

<400> SEQUENCE: 24

Met Glu Lys Leu Thr Asp Leu Asn Tyr Thr Leu Ser Val Ile Thr Leu
1 5 10 15

Met Asn Asn Thr Leu His Thr Ile Leu Glu Asp Pro Gly Met Ala Tyr
20 25 30

Phe Pro Tyr Ile Ala Ser Val Leu Thr Val Leu Phe Ala Leu His Lys
35 40 45

Ala Ser Ile Pro Thr Met Lys Ile Ala Leu Lys Thr Ser Lys Cys Ser
50 55 60

Tyr Lys Val Val Lys Tyr Cys Ile Val Thr Ile Phe Asn Thr Leu Leu
65 70 75 80

Lys Leu Ala Gly Tyr Lys Glu Gln Ile Thr Thr Lys Asp Glu Ile Glu
85 90 95

Lys Gln Met Asp Arg Val Val Lys Glu Met Arg Arg Gln Leu Glu Met
100 105 110

Ile Asp Lys Leu Thr Thr Arg Glu Ile Glu Gln Val Glu Leu Leu Lys
115 120 125

-continued

```
Arg Ile Tyr Asp Lys Leu Thr Val Gln Thr Thr Gly Glu Ile Asp Met
    130                 135                 140

Thr Lys Glu Ile Asn Gln Lys Asn Val Arg Thr Leu Glu Glu Trp Glu
145                 150                 155                 160

Ser Gly Lys Asn Pro Tyr Glu Pro Arg Glu Val Thr Ala Ala Met
                165                 170                 175


<210> SEQ ID NO 25
<211> LENGTH: 175
<212> TYPE: PRT
<213> ORGANISM: Porcine rotavirus A

<400> SEQUENCE: 25

Met Asp Lys Leu Ala Asp Leu Asn Tyr Thr Leu Ser Val Ile Thr Leu
1               5                   10                  15

Met Asn Asp Thr Leu His Ser Ile Ile Gln Asp Pro Gly Met Ala Tyr
            20                  25                  30

Phe Pro Tyr Ile Ala Ser Val Leu Thr Val Leu Phe Thr Leu His Lys
        35                  40                  45

Ala Ser Ile Pro Thr Met Lys Ile Ala Leu Lys Thr Ser Lys Cys Ser
    50                  55                  60

Tyr Lys Val Ile Lys Tyr Cys Met Val Thr Ile Ile Asn Thr Leu Leu
65                  70                  75                  80

Lys Leu Ala Gly Tyr Lys Glu Gln Val Thr Thr Lys Asp Glu Ile Glu
                85                  90                  95

Gln Gln Met Asp Arg Ile Ile Lys Glu Met Arg Arg Gln Leu Glu Met
            100                 105                 110

Ile Asp Lys Leu Thr Thr Arg Glu Ile Glu Gln Val Glu Leu Leu Lys
        115                 120                 125

Arg Ile His Asp Lys Leu Ala Ala Arg Ser Val Asp Ala Ile Asp Met
    130                 135                 140

Ser Lys Glu Phe Asn Gln Lys Asn Ile Arg Thr Leu Asp Glu Trp Glu
145                 150                 155                 160

Ser Gly Lys Asn Pro Tyr Glu Pro Ser Glu Val Thr Ala Ser Met
                165                 170                 175
```